US012700502B2

(12) United States Patent
Ayers et al.

(10) Patent No.: US 12,700,502 B2
(45) Date of Patent: *Aug. 4, 2026

(54) TAGS FOR LOCATING SYSTEM OF MEDICAL FACILITY

(71) Applicant: Hill-Rom Services, Inc., Batesville, IN (US)

(72) Inventors: Brandon Ayers, Carrboro, NC (US); Kenzi Mudge, Raleigh, NC (US); Britten Pipher, Fuquay-Varina, NC (US); John S. Schroder, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 28 days.

This patent is subject to a terminal disclaimer.

(21) Appl. No.: 18/999,128

(22) Filed: Dec. 23, 2024

(65) Prior Publication Data

US 2025/0125047 A1 Apr. 17, 2025

Related U.S. Application Data

(63) Continuation of application No. 18/102,118, filed on Jan. 27, 2023, now Pat. No. 12,217,866.

(Continued)

(51) Int. Cl.
*G16H 40/67* (2018.01)
*G08B 25/01* (2006.01)

(52) U.S. Cl.
CPC ........... *G16H 40/67* (2018.01); *G08B 25/016* (2013.01)

(58) Field of Classification Search
CPC ........ G16H 40/67; G16H 40/20; G16H 40/63; G08B 25/016; G08B 21/0227;

(Continued)

(56) References Cited

U.S. PATENT DOCUMENTS

| | | |
|---|---|---|
| 6,838,992 B2 | 1/2005 | Tenarvitz |
| 8,121,649 B2 | 2/2012 | Shostak |

(Continued)

FOREIGN PATENT DOCUMENTS

CN 107070506 A 8/2017

OTHER PUBLICATIONS

Maged N Kamel Boulos et al; "Real-time locating systems (RTLS) in healthcare: a condenxed primer", International Journal of Health Geographics, Biomed Central Ltd, London, GB, vol. 11, No. 1, Jun. 28, 2012, p. 25, XP021133018, ISSN:1476-072X, DOI: 10.1186/1476-072x-11-25.

*Primary Examiner* — Brian A Zimmerman
*Assistant Examiner* — Cal J Eustaquio
(74) *Attorney, Agent, or Firm* — Price Heneveld LLP

(57) ABSTRACT

A locating system includes a tag with body that has a first button and a second button, a driver configured to determine a type of button press of at least one of the first button and the second button, and a control unit in communication with the driver. The control unit is configured to communicate the type of button press determined by the driver. The tag also includes a transmitter in communication with the control unit. At least one receiver is configured to selectively communicate with the transmitter. A controller is in communication with the at least one receiver. The controller is configured to determine a location of the tag within a predefined area based on information from the at least one receiver, correlate the type of button press from the tag with a message, and generate a notification to communicate the message.

14 Claims, 15 Drawing Sheets

Related U.S. Application Data

(60) Provisional application No. 63/304,775, filed on Jan. 31, 2022.

(58) Field of Classification Search

CPC ............ G08B 21/0272; G08B 21/0286; G08B 21/0291; G08B 21/0294; G08B 13/1427; G01S 5/02213; G01S 5/0295; G01S 2201/01; G06F 1/1626; G06F 3/048; H04W 4/02; H04W 4/33; H04W 4/80; G06Q 10/08

See application file for complete search history.

(56) References Cited

U.S. PATENT DOCUMENTS

| | | | |
|---|---|---|---|
| 8,373,562 | B1 | 2/2013 | Heinze et al. |
| 8,451,098 | B2 | 5/2013 | Posamentier |
| 8,626,246 | B2 | 1/2014 | Shostak |
| 8,787,961 | B2 | 7/2014 | Skalicky |
| 8,957,774 | B2 | 2/2015 | Goldblatt |
| 9,092,963 | B2 | 7/2015 | Fetzer et al. |
| 9,418,530 | B2 | 8/2016 | Rapaport et al. |
| 9,443,415 | B2 | 9/2016 | Nepo |
| 9,473,920 | B2 | 10/2016 | Leahy et al. |
| 9,554,705 | B2 | 1/2017 | Huang |
| 9,633,551 | B2 | 4/2017 | Aljadeff et al. |
| 9,646,473 | B2 | 5/2017 | Ros |
| 9,811,955 | B2 | 11/2017 | Russell et al. |
| 9,996,809 | B2 | 6/2018 | Hall et al. |
| 10,015,839 | B1 | 7/2018 | Depew |
| 10,558,830 | B2 | 2/2020 | Havas et al. |
| 10,643,459 | B2 | 5/2020 | Allen |
| 10,734,110 | B2 | 8/2020 | Smith et al. |
| 10,825,329 | B2 | 11/2020 | Katz et al. |
| 10,872,518 | B2 | 12/2020 | Allen |
| 10,937,286 | B2 | 3/2021 | Daoura et al. |
| 2004/0183682 | A1 | 9/2004 | Tenarvitz |
| 2009/0079549 | A1 | 3/2009 | Ruder |
| 2011/0227726 | A1 | 9/2011 | Lee |
| 2012/0256743 | A1 | 10/2012 | Horton et al. |
| 2012/0270559 | A1 | 10/2012 | Ingerson |
| 2013/0157571 | A1 | 6/2013 | Wondka |
| 2019/0164411 | A1 | 5/2019 | Allen |
| 2020/0075140 | A1 | 3/2020 | Embree et al. |
| 2021/0192592 | A1 | 6/2021 | Callaerts et al. |

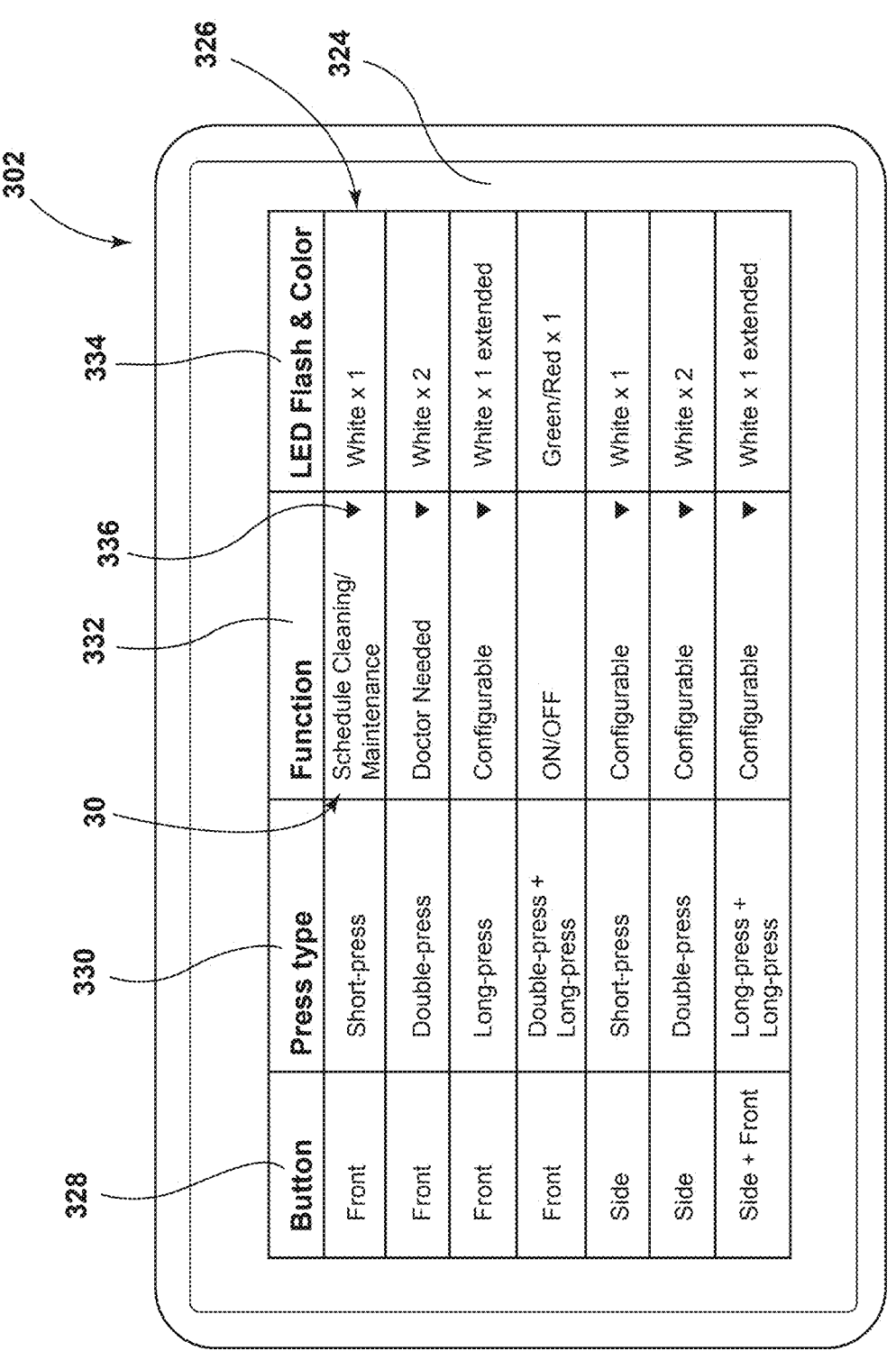

| Button | Press type | Function | | LED Flash & Color |
|--------|------------|----------|---|-------------------|
| Front | Short-press | Schedule Cleaning/ Maintenance | ▶ | White x 1 |
| Front | Double-press | Doctor Needed | ▶ | White x 2 |
| Front | Long-press | Configurable | ▶ | White x 1 extended |
| Front | Double-press + Long-press | ON/OFF | ▶ | Green/Red x 1 |
| Side | Short-press | Configurable | ▶ | White x 1 |
| Side | Double-press | Configurable | ▶ | White x 2 |
| Side + Front | Long-press + Long-press | Configurable | ▶ | White x 1 extended |

382 Activate tag

384 Communicate activation

386 Communicate location

388 Detect motion

390 Communicate motion sensed and updated timing for location information

392 Detect pause in motion

394 Communicate pause sensed and updated timing for location information

396 Communicate notification

TAGS FOR LOCATING SYSTEM OF MEDICAL FACILITY

CROSS-REFERENCE TO RELATED APPLICATIONS

This application is a continuation of U.S. patent application Ser. No. 18/102,118, filed Jan. 27, 2023, now U.S. Pat. No. 12,217,866, entitled, "TAGS FOR LOCATING SYSTEM OF MEDICAL FACILITY," which claims the benefit under 35 U.S.C. § 119 (e) of U.S. Provisional Application No. 63/304,775, filed on Jan. 31, 2022, entitled "TAGS FOR LOCATING SYSTEM OF MEDICAL FACILITY," which is incorporated herein by reference in its entirety.

FIELD OF THE DISCLOSURE

The present disclosure generally relates to badges or tags, and more particularly to badges or tags for a locating system of a medical facility.

SUMMARY OF THE DISCLOSURE

According to one aspect of the present disclosure, a locating system for a medical facility includes at least one tag including a body having at least one button, a driver configured to measure a type of button press for the at least one button, and a transmitter configured to communicate a tag signal. A receiver is disposed in the medical facility. The receiver defines a reception zone for selectively communicating with the transmitter. A controller is in communication with the receiver. The controller is configured to determine a location of the at least one tag based on information from the receiver, correlate a message with the type of button press from the at least one tag, and generate a notification with message information based on the message correlated with the type of button press.

According to another aspect of the present disclosure, a locating system includes a tag including a body having a first button and a second button, a driver configured to determine a type of button press of at least one of the first button and the second button, a control unit in communication with the driver, where the control unit is configured to communicate the type of button press determined by the driver, and a transmitter in communication with the control unit. The transmitter is configured to communicate a tag signal. At least one receiver is configured to selectively communicate with the transmitter. A controller is in communication with the at least one receiver. The controller is configured to determine a location of the tag within a predefined area based on information from the at least one receiver, correlate the type of button press from the tag with a message, and generate a notification to communicate the message.

According to another aspect of the present disclosure, a tag for a locating system includes a front cover including a front button and a side button and a rear cover coupled to the front cover to define an interior. A driver is disposed within the interior and configured to determine a type of button press of the front button and the side button. A transmitter is disposed within the interior. The transmitter is configured to communicate a tag signal to a receiver. A motion sensor is disposed within the interior and is configured to sense movement of said tag. A control unit is in communication with the motion sensor.

These and other features, advantages, and objects of the present disclosure will be further understood and appreciated by those skilled in the art by reference to the following specification, claims, and appended drawings.

BRIEF DESCRIPTION OF THE DRAWINGS

In the drawings:

FIG. 10 is illustrative of an application interface with a configurable table for assigning messages to button presses of a tag, according to the present disclosure;

DETAILED DESCRIPTION

Figure 1:
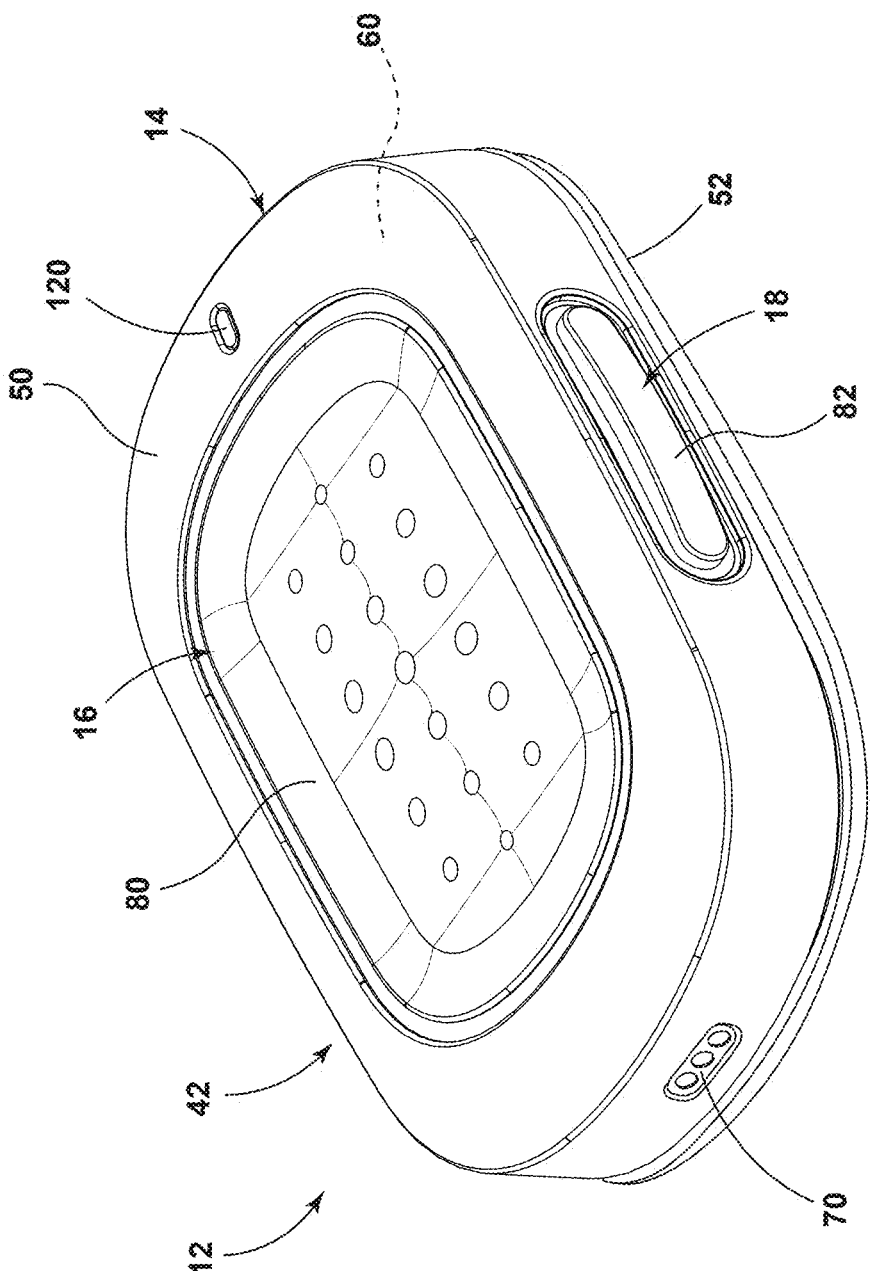
FIG. 1 is a side perspective view of a caregiver tag for a locating system, according to the present disclosure.

The present illustrated embodiments reside primarily in combinations of method steps and apparatus components related to a tag for a locating system of a medical facility. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specifi- cation are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional iden- tical elements in the process, method, article, or apparatus that comprises the element.

With reference to FIGS. 1-16, reference numeral 10 generally designates a locating system that includes a badge or tag 12. The tag 12 includes a body 14 having a first button 16 and a second button 18. The tag 12 includes a driver 20 configured to determine a type of button press of each of the first button 16 and the second button 18. The tag 12 includes a control unit 22 in communication with the driver 20. The control unit 22 is configured to communicate the type of button press determined by the driver 20. The tag 12 also includes a transmitter 24 in communication with the control unit 22. The locating system 10 includes a receiver 26 configured to selectively communicate with the transmitter 24. The locating system 10 also includes a controller 28 in communication with the tag 12 and the receiver 26. The controller 28 is configured to determine a location of the tag 12 within a predefined area based on information from the receiver 26, determine a message 30 that corresponds with the type of button press from the tag 12, and generate a notification 32 with the message 30.

The locating system 10 is configured to have multiple types of tags 12 for monitoring and tracking location and movement of people and equipment or assets within a medical facility 40, as well as for communicating messages 30. In various aspects, the tags 12 are configured as care- giver tags 42, which are generally worn or carried by caregivers during their shift at the medical facility 40, and equipment or asset tags 44, which are fastened or otherwise coupled to equipment, such as medical devices. The locating system 10 is configured to determine the location of the tags 12 and monitor movement of the tags 12. Additionally, each of the caregiver tags 42 and the asset tags 44 may be utilized to convey information or messages 30 about the caregiver, the equipment, the medical facility 40, etc. to other systems of the medical facility 40.

Figure 2:
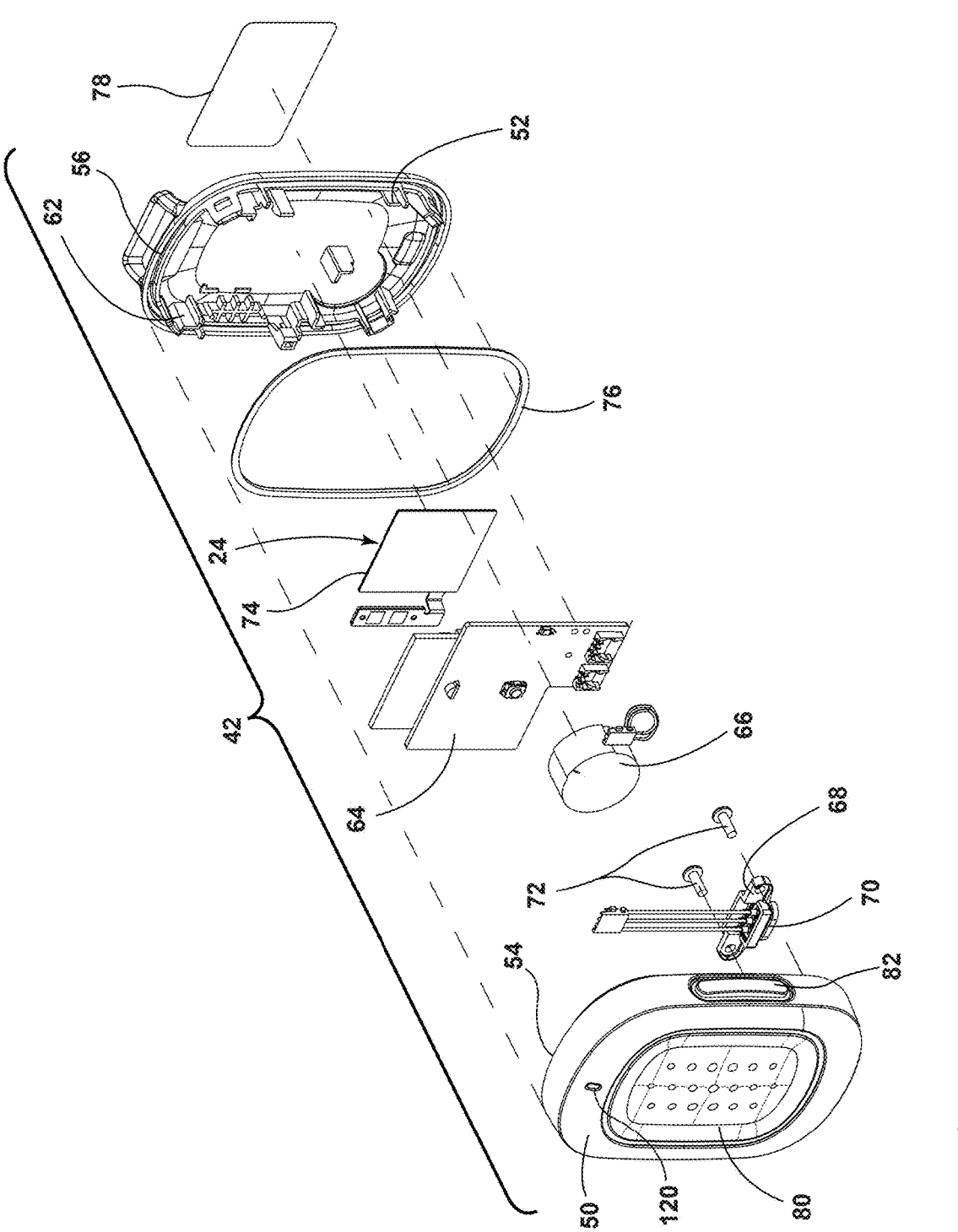
FIG. 2 is an exploded rear perspective view of a caregiver tag, according to the present disclosure.

Referring to FIGS. 1 and 2, the caregiver tag 42, which is worn or carried by a caregiver, is illustrated. The caregiver tag 42 is utilized by the locating system 10 to monitor the location of the caregiver throughout the medical facility 40, as well as communicate messages 30 (FIG. 11) that the caregiver inputs through the caregiver tag 42. The caregiver tag 42 includes the body 14 having a front cover 50 and a rear cover 52. The front and rear covers 50, 52 include mating edges 54, 56 configured to snap engage or form an interference fit to couple the front and rear covers 50, 52 to one another. The front and rear covers 50, 52 couple together to define an interior 60 of the caregiver tag 42, which houses various components.

The rear cover 52 includes supports 62 extending toward the front cover 50 to assist with positioning and aligning the various components within the interior 60 of the caregiver tag 42. The caregiver tag 42 includes a circuit board 64 or circuit board assembly disposed within the interior 60, which may be configured as one or more circuits or a printed circuit board (PCB). In PCB examples, the printed circuit board may be flexible or rigid. The interior 60 of the caregiver tag 42 also houses a power source 66, which is generally configured as a rechargeable battery. The rechargeable battery is coupled with the circuit board 64. The caregiver tag 42 includes a charging assembly 68 operably coupled with a charging port 70. The charging assembly 68 coupled to the charging port 70 with the power source 66 to provide power and charge the power source 66. The various components within the interior 60 of the care- giver tag 42 are coupled via multiple coupling members 72, which may be screws, tapping screws, bolts, or other fas- teners.

The caregiver tag 42 includes a transmitter 74 for com- municating information to the locating system 10 as described further herein. The transmitter 74 may be config- ured as a near field communication (NFC) antenna. Other configurations of the transmitter 74 may be utilized without departing from the teachings herein.

Referring still to FIGS. 1 and 2, the front cover 50 is selectively coupled to the rear cover 52 to enclose the various components within the interior 60. In certain aspects, the front cover 50 and the rear cover 52 may be coupled to one another via an adhesive 76. Additionally or alternatively, a label 78 may be included on an outer surface of the rear cover 52. The label 78 may include a variety of information about the caregiver tag 42, the medical facility 40, the caregiver, etc. Additionally, the label 78 may include an identifier, such as a barcode, that can be scanned to obtain additional information.

The caregiver tag 42 includes a first button 16 on a front or top of the body 14 and a second button 18 on a side of the body 14. The first button 16 may also be referred to as a front button 80, and the second button 18 may also be referred to as a side button 82. In the illustrated example, the buttons 80, 82 are mechanical buttons that may be pressed by the caregiver. However, it is contemplated that other selectable features such as switches, knobs, touch sensitive features, etc. may also be used to provide an input to the caregiver tag 42.

Figure 3:
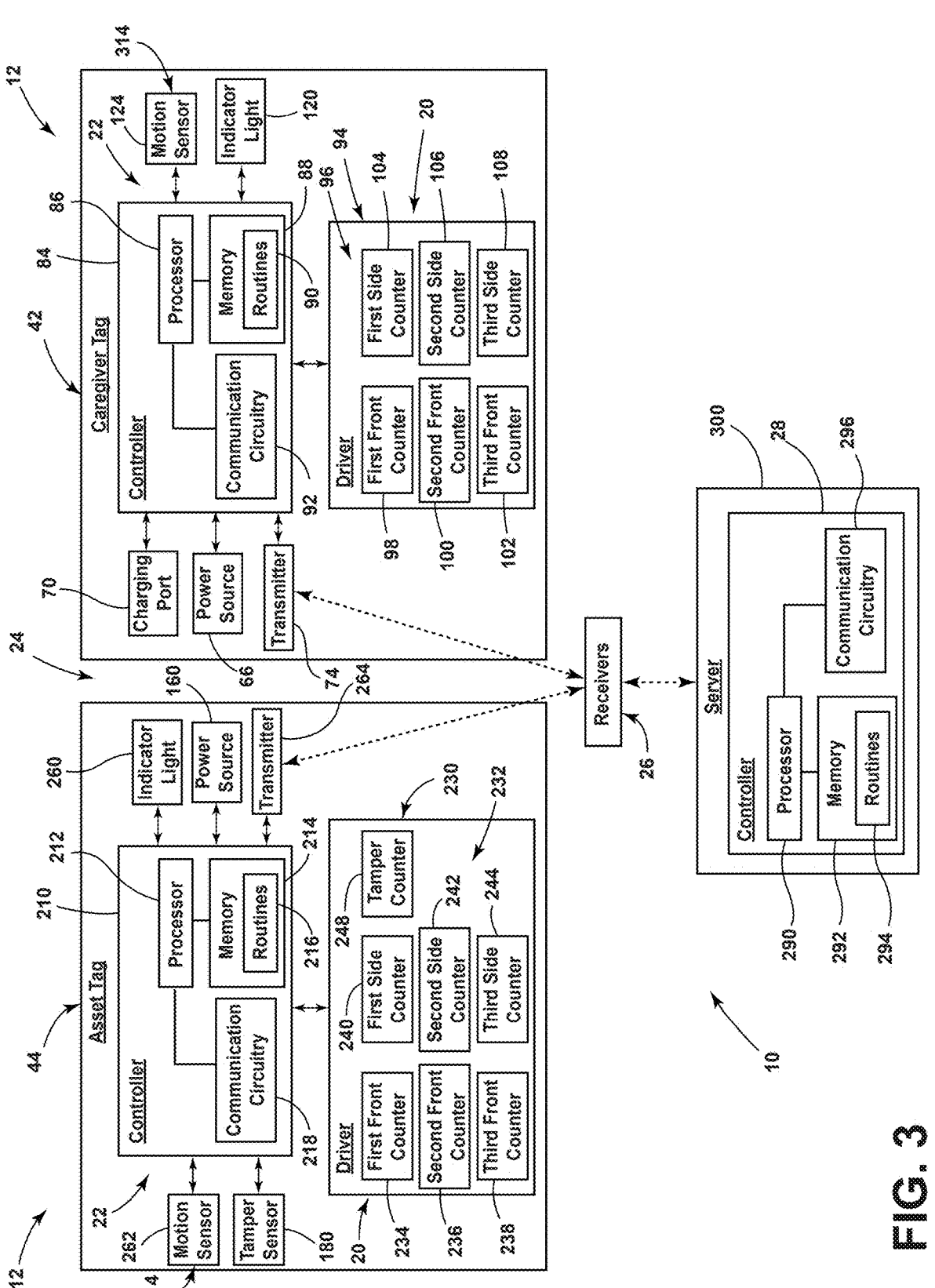
FIG. 3 is a block diagram of a locating system having a caregiver tag and an asset tag in communication with receivers and a controller, according to the present disclosure.

Referring still to FIGS. 1 and 2, as well as FIG. 3, the caregiver tag 42 includes a control unit 84 having the circuit board 64, a processor 86, a memory 88, and other control circuitry. Instructions or routines 90 are stored within the memory 88 and executable by the processor 86. The control circuitry also includes communication circuitry 92 config- ured for bidirectional wired or wireless communication. The control unit 84 includes circuitry configured to perform various inputs or outputs, control, analysis, and other func- tions described herein.

The caregiver tag 42 includes a driver 94 communica- tively coupled with the control unit 84. The driver 94 is configured to determine or measure the type of button press of the front button 80 and the side button 82. Each button 80, 82 may be pressed in a predefined manner, including number of presses, length of press, pattern of presses, etc. For example, a first type of button press may be a single press for a first predefined period of time. A second type of button press may be a double press (e.g., two presses of the respective button 80, 82). Each button 80, 82 press of the double press may be for the first predefined period of time. A third type of button press may be a single press of the respective button 80, 82 for a second predefined amount of time, which is longer than the first predefined period of time. In this way, each of the front button 80 on the side button 82 may be pressed in a single short press (click-and-release), double short presses, and a single long press (click-and-hold). The buttons 80, 82 may also be pressed in a pattern that utilizes presses of one or both the front button 80 and the side button 82 (e.g., side press-front press-side press, etc.) without departing from the teachings herein.

The driver 94 is configured to measure the type of button press utilizing multiple counters 96. In the illustrated example of FIG. 3, the counters 96 include three front counters 98, 100, 102 associated with the front button 80 and three side counters 104, 106, 108 associated with the side button 82. Each type of the button press for each button 80, 82 is counted separately (i.e., by a different counter 96). The counters 96 are configured to be adjusted in response to the corresponding button press (e.g., one type of button press). In certain aspects, the counters 96 are configured to roll in response to the corresponding type of button press and count each roll. For example, each counter 96 may roll between zero and ten or zero and 16 and, upon reaching the highest count, rolls to zero once again. The driver 94 is configured to monitor the roll or adjustment of each counter 96 to determine the type of button press of each button 80, 82. The driver 94 is configured to communicate the type of button press to the control unit 84 for further communication outside of the caregiver tag 42.

Referring still to FIGS. 1-3, the caregiver tag 42 includes an indicator light 120, which is configured to illuminate in response to the button presses. The indicator light 120 may be configured as a confirmation of any button press or as a confirmation of the type of button press entered into the caregiver tag 42. The indicator light 120 is generally disposed on the front cover 50 proximate to the front button 80. In certain aspects, the indicator light 120 is configured to illuminate in a predefined color or predefined pattern based on which button 80, 82 is pressed and the type of button press. The indicator light 120 may include any form of light source. For example, fluorescent lighting, light-emitting diodes (LEDs), organic LEDs (OLEDs), polymer LEDs (PLEDs), laser diodes, quantum dot LEDs (QD-LEDs), solid-state lighting, a hybrid, or any other similar device. Any other form of lighting may be utilized within the caregiver tag 42 without departing from the teachings herein.

Further, various types of LEDs are suitable for use as the indicator light 120, including, but not limited to, top-emitting LEDs, side-emitting LEDs, and others. Moreover, according to various examples, multicolored light sources such as Red, Green, and Blue (RGB) LEDs that employ red, green, blue LED packaging may be used to generate various desired colors of light outputs from a single light source, according to known light color mixing techniques. The color and/or pattern associated with each button 80, 82 and each button press may be personalized or adjusted by the caregiver or the medical facility 40.

Referring still to FIG. 3, the caregiver tag 42 also includes a motion sensor 124 configured to monitor motion and movement of the caregiver tag 42. The motion generally indicates that the caregiver is moving about the medical facility 40. The sensed motion is configured to be communicated to the control unit 84, which may affect the timing of communication from the caregiver tag 42 to the controller 28 of the locating system 10 as described herein. Further, the motion sensor 124 is generally configured to sense when the caregiver taps or shakes the caregiver tag 42, which the motion sensor 124 and/or the control unit 84 is configured to differentiate from movement about the medical facility 40. When the caregiver tag 42 is tapped or shaken, the indicator light 120 may be illuminated in a predefined color or pattern to indicate a charge status of the power source 66. For example, a green light may indicate a high level of charge, a yellow light may indicate a medium level of charge, and a red light may indicate a low level of charge.

Figure 9:
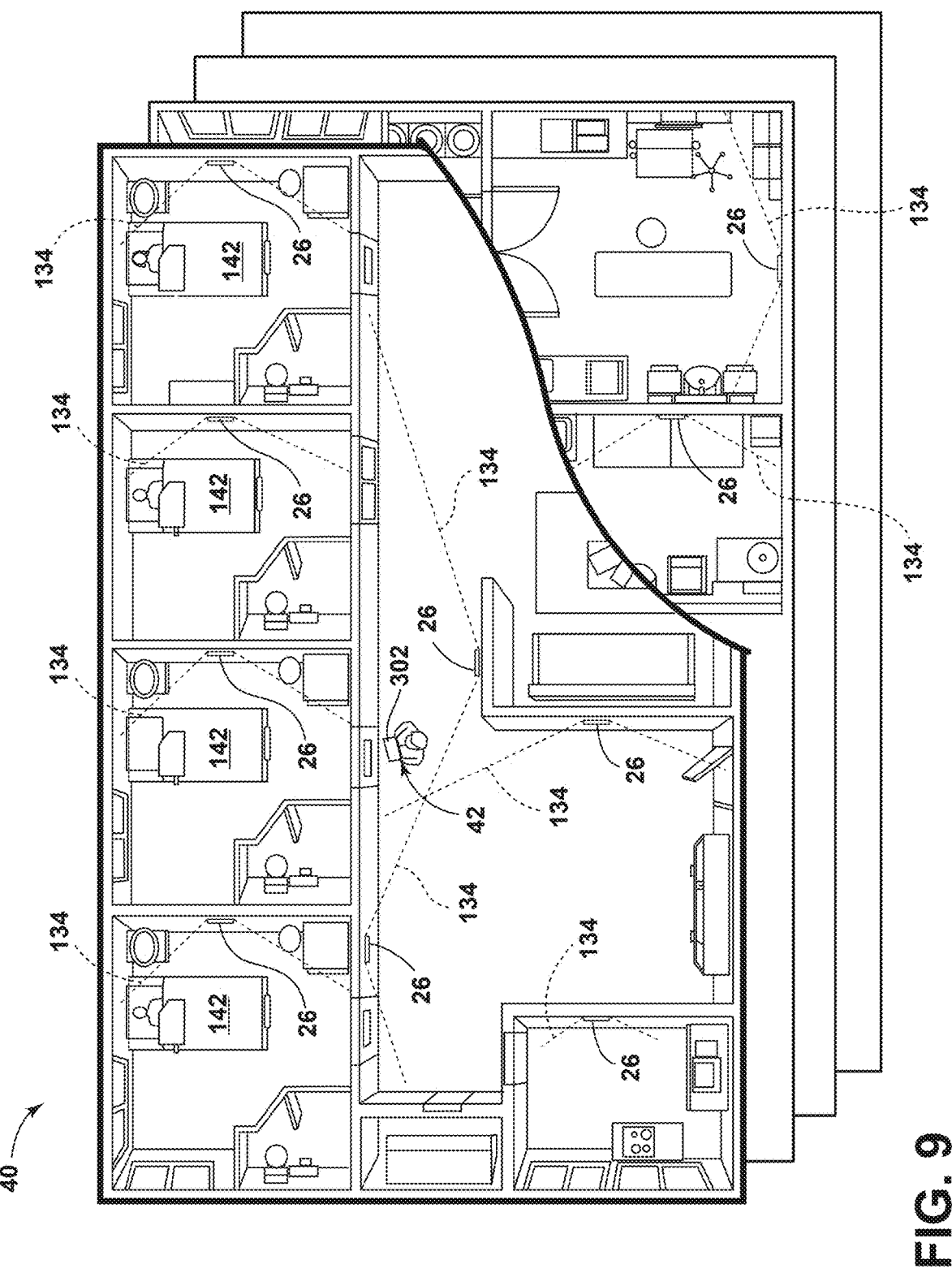
FIG. 9 is illustrative of a receivers disposed about a medical facility, where each receiver defines a reception zone, according to the present disclosure.

The caregiver tag 42 also includes the transmitter 74 configured to selectively communicate with the receiver 26 of the locating system 10. Typically, the medical facility 40 includes multiple receivers 26 positioned about the medical facility 40, with each receiver 26 defining a reception zone 134 (FIG. 9). The transmitter 74 is configured to selectively communicate with the receiver 26 when the caregiver tag 42 is positioned within the corresponding reception zone 134. Using multiple receivers 26, the locating system 10 is configured to track the location of the caregiver tags 42 over the predefined area, which is generally the medical facility 40. The reception zones 134 of the receivers 26 collectively cover at least a substantial portion of the medical facility 40.

Figure 4:
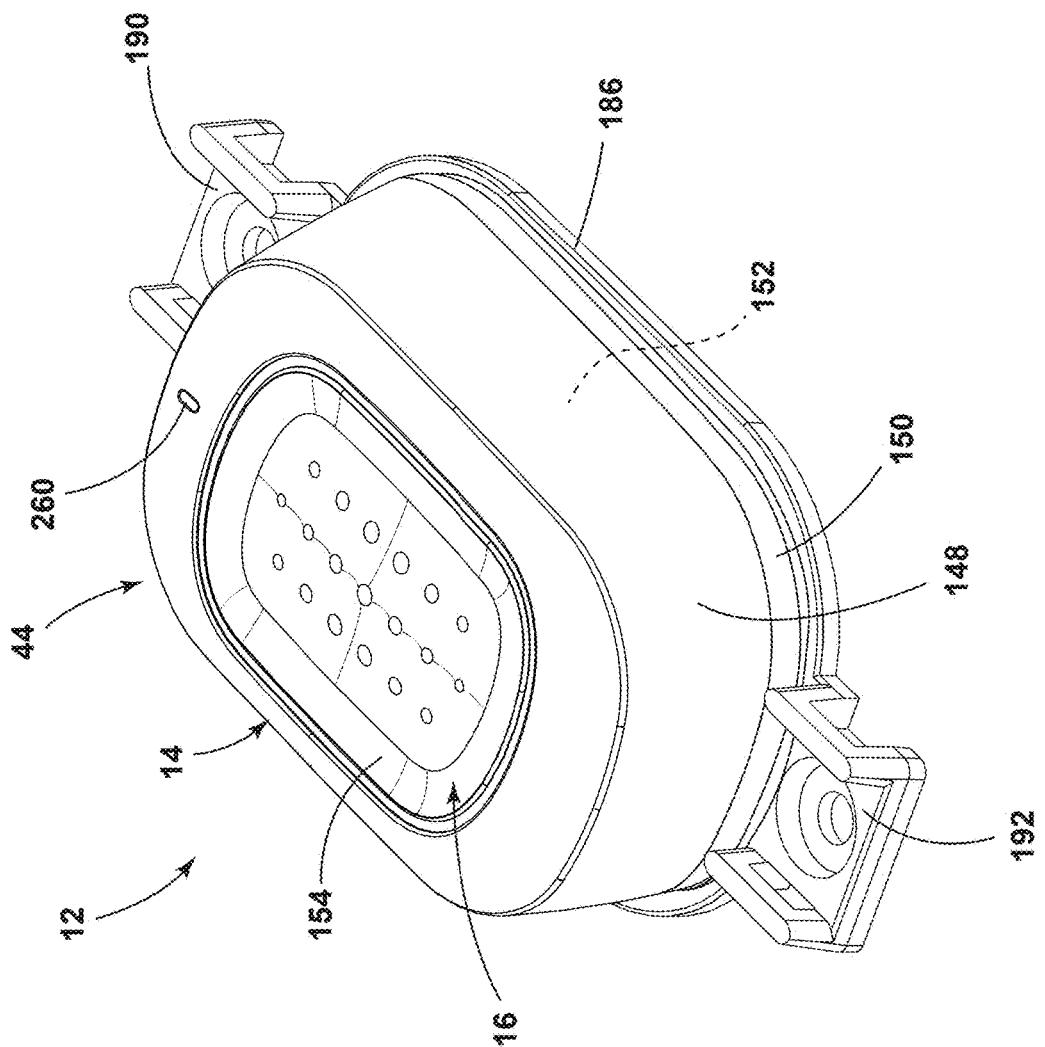
FIG. 4 is a side perspective view of an asset tag for a locating system, according to the present disclosure.
Figure 5:
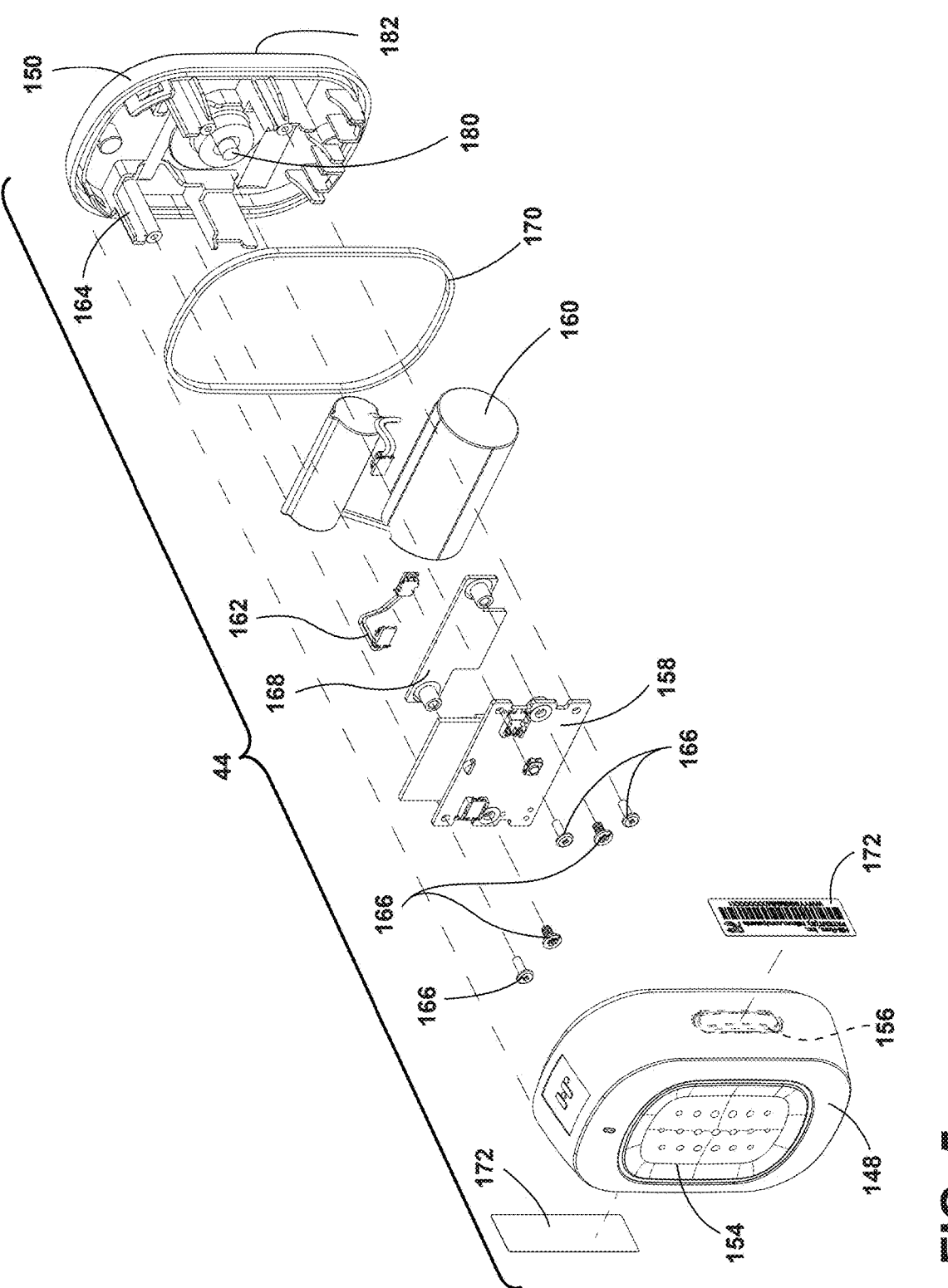
FIG. 5 is an exploded rear perspective view of an asset tag, according to the present disclosure.
Figure 6:
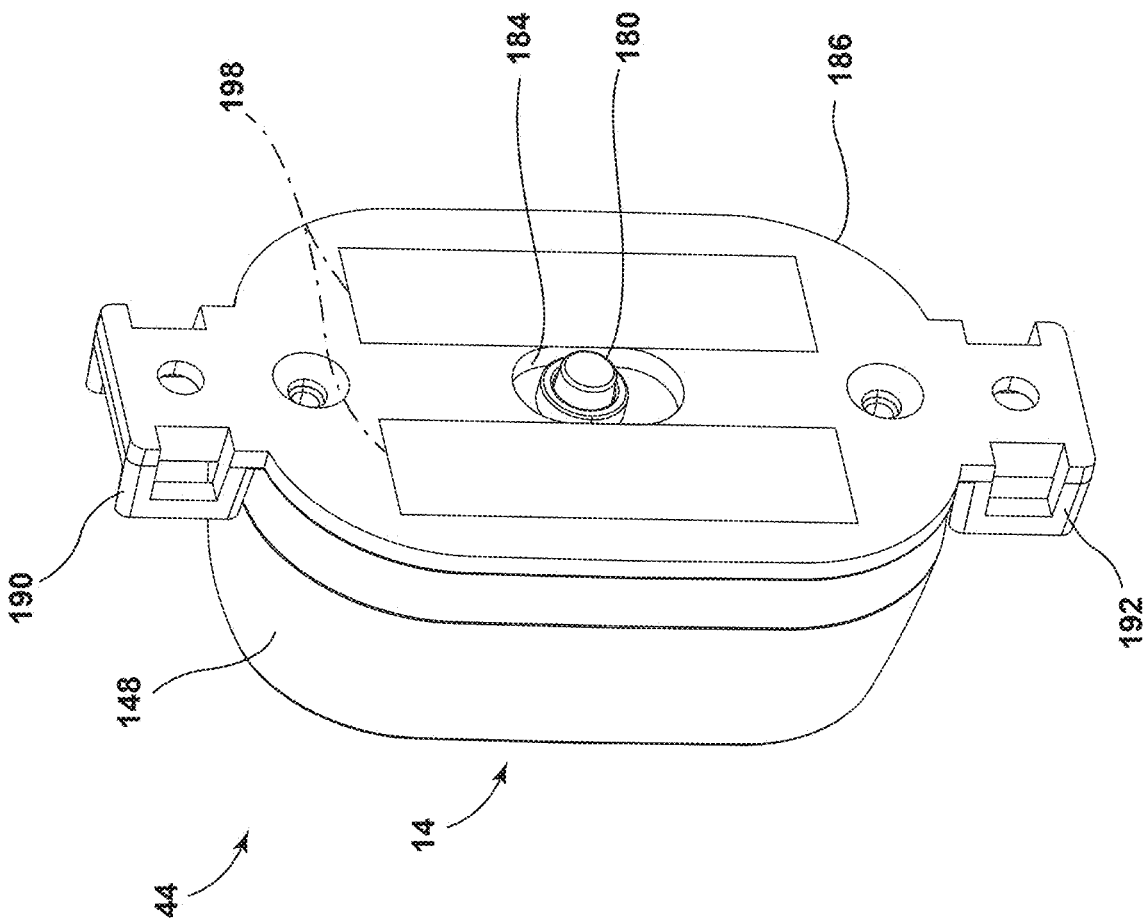
FIG. 6 is a side perspective view of an asset tag having a tamper sensor, according to the present disclosure.

Referring still to FIG. 3, as well as FIGS. 4-6, the locating system 10 also includes the asset tags 44, which are utilized for monitoring and tracking the location and movement of a variety of equipment in the medical facility 40. The equipment may be any practicable device, unit, or system of the medical facility 40, such as, for example, vital sign monitors 140 (FIG. 7), beds 142 (FIG. 7), stretchers, intravenous (IV) pumps, lifts, carts, etc. The asset tag 44 is configured and functions similarly to the caregiver tag 42 described herein.

The asset tag 44 includes a front cover 148 and a rear cover 150, which selectively engage one another to define an interior 152 of the asset tag 44. The body 14 includes at least one of a front button 154 (e.g., the first button 16) and a side button 156 (e.g., the second button 18), which are configured to be pressed by the caregiver to provide an input into the asset tag 44. Other forms of receiving an input (e.g., knobs, switches, touch sensitive features, etc.) may be utilized without departing from the teachings herein. It is also contemplated that the asset tag 44 includes a single button, such as the front button 154, without departing from the teachings herein.

The interior 152 of the asset tag 44 houses various components, including a circuit board 158, which may be configured as one or more circuits, a flexible PCB, or a rigid PCB. The circuit board 158 is coupled to a power source 160 via a cable 162. The power source 160 is generally configured as a battery. Typically, the battery of the asset tag 44 is not rechargeable, but provides power for several years (e.g., about five years). The rear cover 150 includes supports 164 extending toward the front cover 148 to support and position the various internal components of the asset tag 44. The various components within the asset tag 44 may be coupled to one another via coupling members 166, which may be screws, tapping screws, bolts, or other fasteners.

A support plate 168 is generally positioned between the circuit board 158 and the power source 160 to position the circuit board 158 and the cable 162 within the interior 152. The support plate 168 and the circuit board 158 are generally coupled with the coupling members 166. The support plate 168 may include or be configured as an anti-tamper board operably coupled with the tamper sensor 180. The anti-tamper board may be configured to monitor the tamper sensor 180 and/or support the tamper sensor 180.

The front cover 148 and the rear cover 150 are selectively coupled to one another to enclose the interior 152. In various aspects, the front cover 148 and the rear cover 150 may be coupled to one another via adhesive 170. Additionally or alternatively, the front cover 148 may include labels 172. In certain aspects, the asset tag 44 may not include the side button 156, but may include a label 172 on the side of the front cover 148. It is contemplated that the label 172 may be positioned on the side button 156 without departing from the teachings herein. The labels 172 may include a variety of information about the asset tag 44, the device to which the asset tag 44 is coupled, the medical facility 40, etc. Additionally, the labels 172 may include an identifier, such as a barcode, that can be scanned to obtain additional information.

Referring still to FIGS. 3-6, the rear cover 150 includes the tamper sensor 180 extending beyond a rear surface 182 thereof. The tamper sensor 180 is configured to extend through an aperture 184 defined in a bracket 186 that is coupled to the rear cover 150 via additional coupling members. The bracket 186 is coupled to the rear cover 150 for engaging equipment. The bracket 186 is configured to couple the asset tag 44 to a piece of equipment or a medical device within the medical facility 40. The bracket 186 includes two opposing coupling portions 190, 192, which extend beyond the rear cover 150 to receive coupling members for fastening the bracket 186 to the equipment. The coupling portions 190, 192 may protrude or be offset from the remainder of the bracket 186 to form ledges that can assist in positioning the asset tag 44 relative to the bracket 186.

Additionally or alternatively, the asset tag 44 may be coupled to the piece of equipment using a fastening member, such as a zip tie or similar feature. The fastening members generally extend through opposing slots defined in the coupling portions 190, 192, apertures defined in the coupling portions 190, 192, or combinations thereof.

In certain aspects, the asset tag 44 may also include adhesive pads 198 configured selectively engage a surface of the equipment and one or both of the rear cover 150 and the bracket 186. The adhesive pads 198 may assist with coupling asset tag 44 to the piece of equipment, as well as for providing stability to further couple the asset tag 44 to the equipment via the coupling members and/or the fastening member. The adhesive pads 198, the coupling members and/or the fastening member are configured to secure the asset tag 44 to the piece of equipment in a manner that prevents inadvertent or accidental removal of the asset tag 44. The asset tag 44 may be configured to remain activated while coupled with the piece of equipment, which may be advantageous for preventing theft or unauthorized movement of specific equipment.

The asset tag 44 includes the tamper sensor 180 operably coupled to the bracket 186 and configured to sense when the asset tag 44 is coupled to or engaged with a piece of equipment and when the asset tag 44 is disengaged from the equipment. In certain aspects, the tamper sensor 180 may be a button or adjustable feature, which is pressed when abutting the equipment and released when the asset tag 44 is removed from the equipment. Other configurations of sensors may be utilized without departing from the teachings herein. The tamper sensor 180 is configured to sense if or when the asset tag 44 is removed from the equipment, which is advantageous for preventing or monitoring unauthorized removal of the asset tag 44. Once the asset tag 44 is placed on the piece of equipment, the tamper sensor 180 is pressed or adjusted, which is reported to the controller 28.

The asset tag 44 includes a control unit 210 having the circuit board 158, a processor 212, a memory 214, and other control circuitry. Instructions or routines 216 are in the memory 214 and executable by the processor 212. The control circuitry may also include communication circuitry 218 configured for bidirectional wired or wireless communication. The control unit 210 includes circuitry configured to perform various inputs or outputs, control, analysis, and other functions described herein.

The asset tag 44 includes the front button 154 and the side button 156, which are configured to operate in a similar manner as the caregiver tag 42 described herein. The asset tag 44 also includes a driver 230, which monitors adjustments of multiple counters 232 to determine or measure the type of button press for each of the buttons 154, 156. The asset tag 44 includes multiple counters 234, 236, 238 associated with the front button 154 and multiple counters 240, 242, 244 associated with the side button 156. Each counter 232 is configured to adjust or roll in response to a predefined type of button press for one of the front button 154 and the side button 156. For example, the asset tag 44 illustrated in FIG. 3 is configured for three types of button presses (e.g., single short press, double short press, single long press) for each of the front button 154 and the side button 156 and therefore includes the three front counters 234, 236, 238 and the three side counters 240, 242, 244. Each counter 232 is configured to roll to a new or next number for the corresponding type of button press for the respective button 154, 156, which is communicated by the driver 230 to the control unit 210.

Referring still to FIG. 3, the asset tag 44 also includes an additional tamper counter 248. The tamper counter 248 is associated with the tamper sensor 180. Each adjustment of the tamper sensor 180 or change sensed by the tamper sensor 180 is counted by the tamper counter 248. The tamper counter 248 is configured to adjust or roll to a new or next number with each change of the tamper sensor 180. The driver 230 is configured to monitor the count of the tamper sensor 180 and communicate any adjustment to the control unit 210. The tamper counter 248 is advantageous for monitoring when the asset tag 44 is removed from the equipment.

Further, even if the asset tag 44 is recoupled to the equipment, the tamper counter 248 is adjusted in response to the removal and the recoupling, providing an indication that the asset tag 44 has been removed or otherwise tampered. Additionally or alternatively, the asset tag 44 is configured to monitor if and how often the asset tag 44 is removed from the equipment. It is contemplated that one of the types of button presses may correspond with the message 30 (FIG. 11) that the asset tag 44 is being removed from the equipment, in which case the tamper counter 248 is adjusted but the control unit 210 may not communicate the removal of the asset tag 44 to the controller 28 of the locating system 10.

With reference still to FIG. 3, similar to the caregiver tag 42, the asset tag 44 includes an indicator light 260 configured to illuminate in response to multiple functions of the asset tag 44, including button presses and charge status level of the power source 160. The indicator light 260 may illuminate in predefined color or predefined pattern based on which button 154, 156 is pressed and what type of button press occurs.

The indicator light 260 may include any form of light source. For example, fluorescent lighting, LEDs, OLEDs, PLEDs, laser diodes, QD-LEDs, solid-state lighting, a hybrid, or any other similar device. Any other form of lighting may be utilized within the asset tag 44 without departing from the teachings herein. Further, various types of LEDs are suitable for use as the asset tag 44, including, but not limited to, top-emitting LEDs, side-emitting LEDs, and others. Moreover, according to various examples, multicolored light sources such as RGB LEDs that employ red, green, blue LED packaging may be used to generate various desired colors of light outputs from a single light source, according to known light color mixing techniques.

The asset tag 44 also includes a motion sensor 262 for monitoring movement and motion of the asset tag 44 and, consequently, the equipment to which the asset tag 44 is coupled. The motion sensor 262 and/or the control unit 210 may be configured to differentiate movement of the asset tag 44 from shaking or tapping the asset tag 44. Shaking or tapping the asset tag 44 may result in the illumination of the indicator light 260 to indicate the charge level of the power source 160.

Referring still to FIG. 3, the asset tag 44 also includes a transmitter 264, which is configured to communicate with the receivers 26 throughout the medical facility 40 as described herein. The communication between the transmitter 264 and the receivers 26 allows the locating system 10 to track the movement of the asset tags 44 throughout the medical facility 40.

Figure 7:
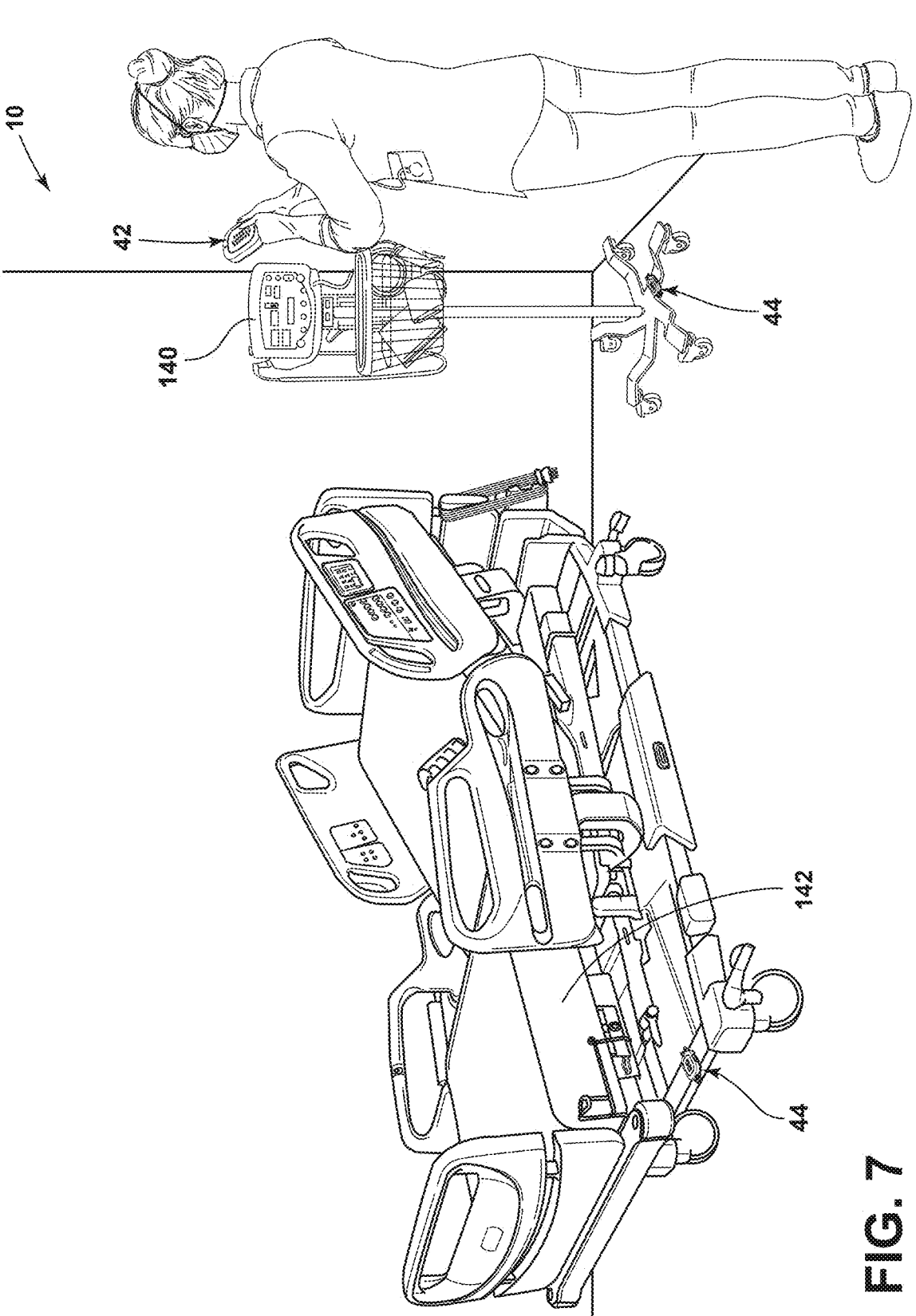
FIG. 7 is a side perspective view of a bed with an asset tag and a vital signs monitor with an asset tag proximate to a caregiver with a caregiver tag, according to the present disclosure.

With reference to FIGS. 3 and 7, the caregiver tag 42 and the asset tag 44 may operate in a substantially similar manner. The caregiver tag 42 may be smaller in size compared to the asset tag 44, allowing for the caregiver tag 42 to be carried or worn by the caregiver. Further, the asset tag 44 may include the bracket 186 for coupling the asset tag 44 to the piece of equipment, such as the exemplary vital signs monitor 140 and bed 142. Moreover, the caregiver tag 42 is configured to be rechargeable, while the asset tag 44 includes the power source 160 that lasts several years.

Figure 8:
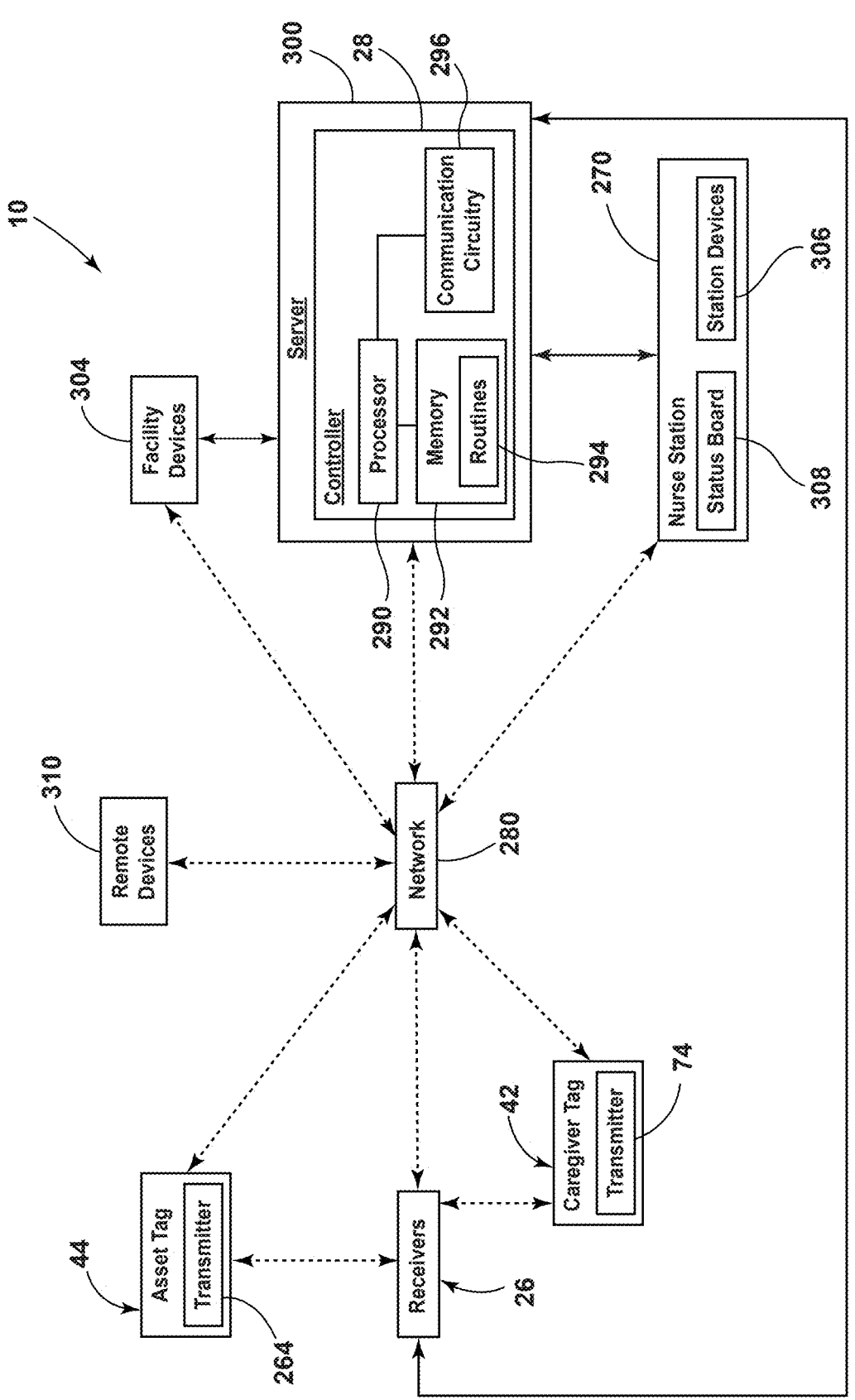
FIG. 8 is a block diagram of a locating system of a medical facility, according to the present disclosure.

With reference still to FIG. 3, as well as to FIGS. 8 and 9, the locating system 10 includes the caregiver and asset tags 42, 44, collectively referred to herein as the tags 12. The receivers 26 are arranged about the medical facility 40 and are configured to selectively communicate with each tag 12 when the tags 12 are located in the respective reception zone 134. The receivers 26 may be located in each patient room, surgical suite, imaging room, unit, or area throughout the medical facility 40. Additional receivers 26 may be located at nurse call stations 270 or within hallways of the medical facility 40. The reception zones 134 collectively encompass at least a substantial portion of the medical facility 40.

The locating system 10 is generally configured as a real-time locating and tracking system (RTLS) to track caregivers and equipment throughout the medical facility 40. The tags 12 and the receivers 26 are each configured to communicate directly or indirectly with the controller 28. The transmitters 24 (collectively including the transmitters 74, 264) of the tags 12 are configured to transmit tag signals to the receivers 26 positioned at various locations of the medical facility 40. The tag signals from the tag 12 each include a unique tag identification (ID) code or number that is correlated by the controller 28 to the identity of the caregiver or the identity of the equipment with which the tag 12 has been assigned.

The receivers 26 each transmit receiver information, such as a receiver ID, along with tag information, such as the tag ID of any tags 12 within the reception range of the particular receiver 26, to the controller 28 via a communication network 280. The receiver ID is correlated by the controller 28 to particular locations (e.g., room, unit, hallway, etc.) of the medical facility 40. Accordingly, based on the transmission from various receivers 26, the location of the equipment or caregivers with associated tags 12 may be monitored. It is also contemplated that certain patients may wear or carry patient tags 12 to track the movement of patients about the medical facility 40 without departing from the teachings herein.

The tags 12 and the receivers 26 may implement a variety of wireless communication technologies to communicate with one another and/or the controller 28 to track the location of the caregivers and equipment within the medical facility 40. Exemplary wireless technologies may include radiofrequency (RF), Wi-Fi (i.e., 802.11), Bluetooth®, Bluetooth® low energy (BLE), Thread, Ultra-Wideband, Z-wave, ZigBee, Infrared (IR), ultrasonic, etc.

Referring still to FIGS. 8 and 9, the receivers 26 are configured to receive the wireless signal (i.e., the tag signals) from the tags 12 and communicate the tag signal and/or the tag ID, as well as other information, to the controller 28 via network infrastructure, such as the communication network 280. The controller 28 may then process the information, which generally includes the receiver ID and the tag ID, to determine the location of the tags 12 in the medical facility 40. The controller 28 may also process the information to correlate the type of button press to a designated message 30 as described herein.

The tag signal or other information from the tag 12 may be communicated from to the receiver 26 and then to the controller 28. Alternatively, the tag signal or information from the tag 12 may be communicated directly to the controller 28, which may or may not utilize the communication network 280. The controller 28 has a processor 290, a memory 292, and other control circuitry. Instructions or routines 294 are stored within the memory 292 and executable by the processor 290. The control circuitry may include communication circuitry 296 configured for bidirectional wired or wireless communication. The controller 28 includes circuitry configured to perform various inputs or outputs, control, analysis, and other functions described herein. The controller 28 may be included in a server 300, which may be a local server 300 of the medical facility 40 or a remote server 300 off-site from the medical facility 40.

Referring still to FIGS. 8 and 9, the receivers 26 are configured to communicate with the controller 28 via the communication network 280. The information may be communicated in a single direction from the receivers 26 to the controller 28 or bidirectionally depending on the configuration of the locating system 10. The communication network 280 may include a combination of wired connections (e.g., Ethernet), as well as wireless connections, which may include the wireless communication network 280. The communication network 280 may include a variety of electronic devices, which may be configured to communicate over various wired or wireless communication protocols. The communication network 280 may include a wireless router through which the remotely accessed devices may be in communication with one another, as well as the server 300.

The communication network 280 may be implemented via one or more direct or indirect nonhierarchical communication protocols, including but not limited to, Bluetooth®, Bluetooth® low energy (BLE), Thread, Ultra-Wideband, Z-wave, ZigBee, etc. Additionally, the communication network 280 may correspond to a centralized or hierarchal communication network 280 where one or more of the devices communicate via the wireless router (e.g., a communication routing controller). Accordingly, the communication network 280 may be implemented by a variety of communication protocols, including, but not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area network, Ethernet, etc. By flexibly implementing the communication network 280, the various devices and servers 300 may be in communication with one another directly via the wireless communication network 280 or a cellular data connection.

Referring still to FIG. 8, the memory 292 of the locating system 10 may include a database that stores correlated tag IDs, location IDs, caregiver names, location names, equipment names, etc. in a table or array. The software (e.g., routines 294) may utilize information communicated to the server 300 by the receivers 26 and/or the tags 12, as well as information stored within the server 300.

In certain aspects, the receivers 26, the tags 12, or both may be configured for bidirectional communication. In such examples, the receivers 26 may transmit signals to the tags 12 and the tags 12 make communicate directly to the controller 28. For example, the location or receiver ID may be transmitted to the tag 12, which then communicates the receiver ID and the tag ID to the controller 28 for processing.

Referring still to FIG. 8, the information received by the controller 28 generally includes the ID information, as well as additional button press information determined by the driver 20 (which collectively includes the drivers 94, 230) of the respective tag 12. The button press information generally includes button counter values determined by the driver 20 of the respective tag 12 using the counters 96, 232. The button press information may be included in the tag signal or may be separately communicated information. The locating system 10 may be programmed to correlate various messages 30 (FIG. 11) to different types of button press information. The messages 30 may include updates, information, tasks, actions, requests, etc. The message 30 may be configured (e.g., assigned, adjusted, etc.) by those at each medical facility 40. A message or assignment input may be received through an application interface 302 (FIG. 10) on a facility device 304, from a station device 306 or status board 308 at the nurse call station 270, from a remote device 310, etc.

Figure 11:
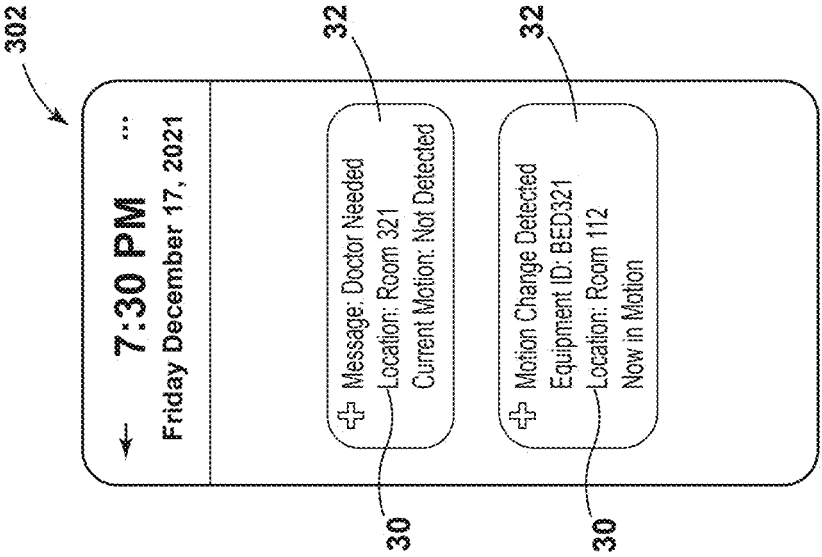
FIG. 11 is illustrative of an application interface with notifications from a locating system, according to the present disclosure.

The caregivers or administrators at the medical facility 40 may assign the types of button presses to certain messages 30 (FIG. 11). In this way, the locating system 10 may be customized by the medical facility 40, which may be advantageous for providing efficient communication via the locating system 10. The tags 12 may communicate the type of button press directly or indirectly to the controller 28, which correlates the message 30 with the button press information. The tags 12 each support button press combinations of the individual buttons 16, 18 (i.e., multiple types of presses of the first button 16 and multiple types button presses of the second button 18) and may support combinations between the two buttons (e.g., first-second-first, second-first second, first-first-second, etc.).

The drivers 20 of each of the tags 12 are configured to determine or measure the type of button press for the first button 16 and the second button 18, which collectively include the front buttons 80, 154 and the side buttons 82, 156, respectively. The drivers 20 communicate the type of button press, which includes which button 16, 18 was pressed, to the respective control unit 22 (collectively including control units 84, 210). The type of button press and the pressed button 16, 18 is communicated wirelessly to the controller 28 of the locating system 10, either directly or through the receivers 26. Typically, the button press information, including the button counter values, are communicated regularly or at predefined intervals to the controller 28.

The controller 28 is configured to process the type of button press information and correlate the button press information with the message 30 stored in the memory 292 of the controller 28. The controller 28 is configured to determine the type of button press based on the received button information. The controller 28 is configured to compare newly received button press information with previously received button information. If the button counter values in the newly received button press information is different than the last known button counter values from previous button press information, the controller 28 determines that a button press has occurred and determines the type of button press. The comparison between the newly received button press information and the previous or last known button press information minimizes or prevents missed button press communication, which may be caused by signal collisions, interference, attenuation, etc. In certain aspects, the controller 28 is configured to utilize the difference between the last known counter values and the newly received counter value to know how many times the buttons 16, 18 were pressed (i.e., the type of button press or the pattern of button press) since the last time a transmission of the button press information was successful.

With reference again to FIG. 3 and still to FIG. 8, each tag 12 includes the motion sensors 124, 262, which are collectively referred to as motion sensors 314. Each tag 12 may adjust operation in response to the sensed motion. For example, when the tag 12 is stationary, the tag 12 may communicate the wireless signal (the tag signal) to the receivers 26 at first predefined time intervals. When the tag 12 is in motion, the tag 12 may communicate the tag signal to the receivers 26 at second predefined time intervals, which are shorter than the first predefined time intervals. Accordingly, the tag signal is emitted more frequently when the tag 12 is in motion to more efficiently track the location of the tags 12.

The receivers 26 may immediately and automatically communicate with the controller 28 in response to receiving the tag signal. In this way, the locating system 10 may receive information (e.g., receiver ID, tag ID, etc.) for each tag 12 at quicker intervals when the tags 12 are moving compared to when the tags 12 are stationary. This allows the locating system 10 to correlate the received information with the location and track the movement of the tags 12 about the medical facility 40. It is contemplated that the intervals in which the tags 12 emit the wireless signal may also change based on the speed of the tag 12, such that faster motion results in shorter intervals.

The control units 22 of the tags 12 receive information from the motion sensors 314. Each control unit 22 is configured to receive the sensed motion information from the motion sensor 314 and communicate the change in motion to the controller 28. This motion information may be included in the tag signal or may be separately communicated information. For example, when the motion sensor 314 senses that the respective tag 12 is moving after being stationary, the control unit 22 is configured to communicate with the controller 28 that the tag 12 is now in motion. Along with the update that the tag 12 is now in motion, the control unit 22 communicates timing intervals in which the tag 12 will communicate the wireless signal. Accordingly, the tag 12 communicates the wireless signal will be emitted to the receiver 26 at first predefined intervals. The controller 28 is then configured to receive the information from the receivers 26 at the first predefined intervals and monitors whether or not the updated information is received at each interval.

When the tag 12 stops moving for a predefined period of time, the control unit 22 is configured to communicate to the controller 28 that the tag 12 is now stationary and will be communicating the wireless signal at second longer predefined intervals. The controller 28 is then configured to receive the updated information from the receivers 26 about the tag 12 at the second predefined intervals and monitors whether the updated information is received at each interval. Similar communication and updates may be utilized based on the speed of the movement of the tags 12 without departing from the teachings herein. In such examples, a change in speed or a change in speed over a predefined threshold may trigger an update regarding the speed of the tag 12 and updated timing intervals.

The notification to the controller 28 about the adjustment of the timing intervals for emitting the wireless signal is advantageous for monitoring communication with the tags 12, as well as determining whether to generate an alert 320 (FIG. 12) about a missed update at a certain timing interval. For example, if the controller 28 is monitoring for updates and the updated information is not received for a predefined number of intervals, the controller 28 is configured to generate the alert 320 to indicate that the tag 12 that did not communicate the update is no longer in communication with the receivers 26 and/or the controller 28 (e.g., free of communication with the locating system 10). The lack of communication may be for a variety of reasons, including theft, power loss, loss of reception, etc., and the caregiver may investigate.

Referring still to FIG. 8, the control unit 22 is configured to communicate the type of button press when in communication with the receivers 26 and/or the controller 28. If there is a loss of reception, such as in an elevator or a stairwell, the control unit 22 is configured to communicate the button press information upon re-connecting with the receivers 26 and/or controller 28 to minimize missed information. The tag 12 is configured to determine the type of button press without connectivity to the locating system 10 based on the adjustment of the counters 96, 232 (FIG. 3), respectively.

In certain aspects, the button press information communicated from the tag 12 may include a timestamp. The controller 28 may compare the timestamp of the received button press information with a current time to determine an elapsed time. The generated notification 32 (FIG. 11) based on the message 30 associated with the type of button press may include the elapsed time. Alerting the caregiver of the elapsed time may be advantageous for the caregiver to prioritize different notifications 32.

The tags 12 and/or the receivers 26 may be configured to communicate information to the controller 28 without confirmation in a single-direction communication. Alternatively, the controller 28 may communicate a confirmation of the received information to the receivers 26 and/or the tags 12. The confirmation to the tag 12 may be through the receiver 26 or directly to the tag 12. The confirmation may be indicated to the caregiver via the respective indicator light 120, 260 illuminating, for example, in a predefined color or pattern.

Additionally or alternatively, certain types of information may be communicated to the controller 28 multiple times to produce a redundancy and reduce missed information. For examples, each status change or change in circumstances of the tags 12 may be communicated multiple times. The status change may include change in motion, deactivation due to an input, deactivation due to impending power loss, activation, etc. When the tag 12 is to be deactivated or turned off, the tag 12 communicates that information to the controller 28 and the controller 28 stops monitoring for updates at the predefined intervals.

Referring to FIG. 10, an exemplary application interface 302 is illustrated with a configuration screen 324. The configuration screen 324 includes a table 326 having a button listing 328, a press type listing 330, a function listing 332 of messages 30, and a light listing 334. The table 326 shows which types of button presses of which buttons 16, 18 correspond with the message 30 and the type of illumination of the indicator light 120, 260. The information in the table 326 is merely exemplary and not meant to be limiting.

Proximate to each message 30 in the function listing 332 is an expand icon 336, which may allow a drop-down menu of different messages 30, a text box to type a message 30, etc. The medical facility 40 may choose the message 30 (e.g., function) associated with each type of button press for each button 16, 18. In this way, the application interface 302 may receive an assignment input where the caregiver assigns certain messages 30 with each button 16, 18 and type of button press. Examples of messages 30 may include a distress call, a distress alert, a request for cleaning, a request for a doctor, an urgency level, schedule maintenance, a ready-to-pair mode, on/off, etc. Each message 30 may be a preset message 30, predefined message information, or predefined types or categories of information.

The messages 30 may be configured and customized by those of the medical facility 40 and may be changed. Each message 30 for the asset tag 44 may be adjustable separate from the caregiver tags 42. Further, the messages 30 for the button presses on the asset tag 44 may be the same, different, or overlap as those for the caregiver tag 42. In certain aspects, each caregiver tag 42 in the medical facility 40 may have the same messages 30 and each asset tag 44 in the medical facility 40 may have the same messages 30. Alternatively, the messages 30 may be customizable and personalized for each caregiver, each caregiving team, each type of equipment, each piece of equipment, etc. The messages 30 may be adjusted, personalized, etc. through the application interface 302. The table 326 may be stored in or accessed by the controller 28 to associate the received button press information with the designated message 30.

The table 326 may also include an assignment as to which application interface 302 on which to display the message 30 or message information, such as the station device 306, the status board 308 at the nurse call station 270, the remote device 310, the facility device 304, etc. Further, certain groups of people may be assigned to each function or message 30. For example, if the message 30 is to call for a doctor, all doctors within the medical facility 40 or within the unit in which the tag 12 is located may receive the notification 32. If the message 30 is to request security, a security team for the medical facility 40 may receive the notification 32. Additionally, caregivers in certain locations, as determined by the locating system 10, may receive the notification 32. Those who receive the notification 32 may be configurable similar to the functions associated with each type of button press.

Referring to FIG. 11, the controller 28 (FIG. 3) is configured to generate the notification 32 based on the assigned message 30 and/or to include the message 30 or related message information. The notification 32 is configured to be communicated to the application interface 302 for viewing by the caregiver, as illustrated in FIG. 11. The notification 32 may include the predefined message 30 or categories of information corresponding with the message 30. The notification 32 may differ based on the type of tag 12, the location of the tag 12, elapsed time between the button press and reception to the controller 28, etc. The notification 32 may also include information about the current location of the tag 12 that communicated the button press information from the caregiver or whether the tag 12 was in motion when the notification 32 was generated. The information illustrated in the notification 32 of FIG. 11 is merely exemplary and any practicable information may be included without departing from the teachings herein.

Figure 12:
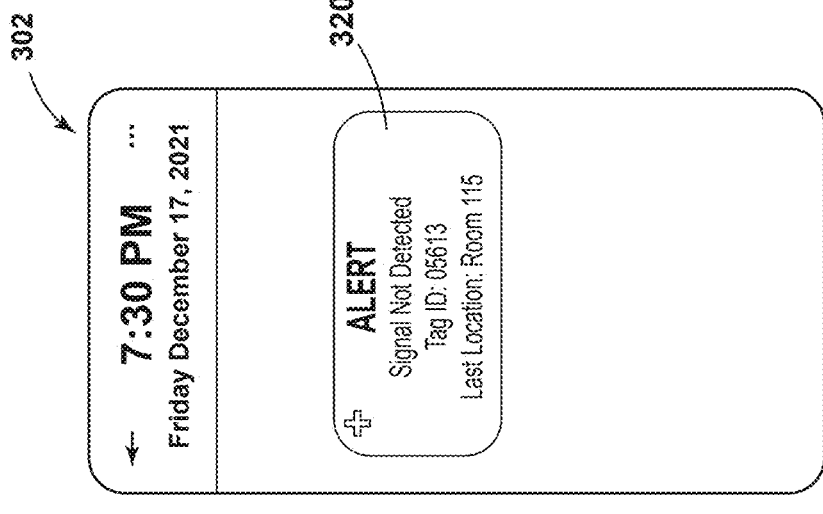
FIG. 12 is illustrative of an application interface with an alert from a locating system, according to the present disclosure.

Referring to FIG. 12, the controller 28 (FIG. 3) monitors the signals received from the tags 12 to determine the location and monitors when an updated or subsequent signal is not received at the predefined intervals. When the subsequent signal or multiple subsequent intervals are not received at the predefined intervals, the controller 28 is configured to generate the alert 320 and communicate the alert 320 to the application interface 302, as illustrated in FIG. 12. The alert 320 can include a variety of information, including the tag ID, the last location of the tag 12, whether the tag 12 was in motion prior to the missed intervals, etc. The information illustrated in the alert 320 of FIG. 12 is merely exemplary and any practicable information may be included without departing from the teachings herein. Those who receive the alert 320 may be designated and/or configurable by the medical facility 40 based on the type of alert 320, the location of the alert 320, etc. The alert 320 and alert information can be configurable in a similar process as the notification 32.

Figure 13:
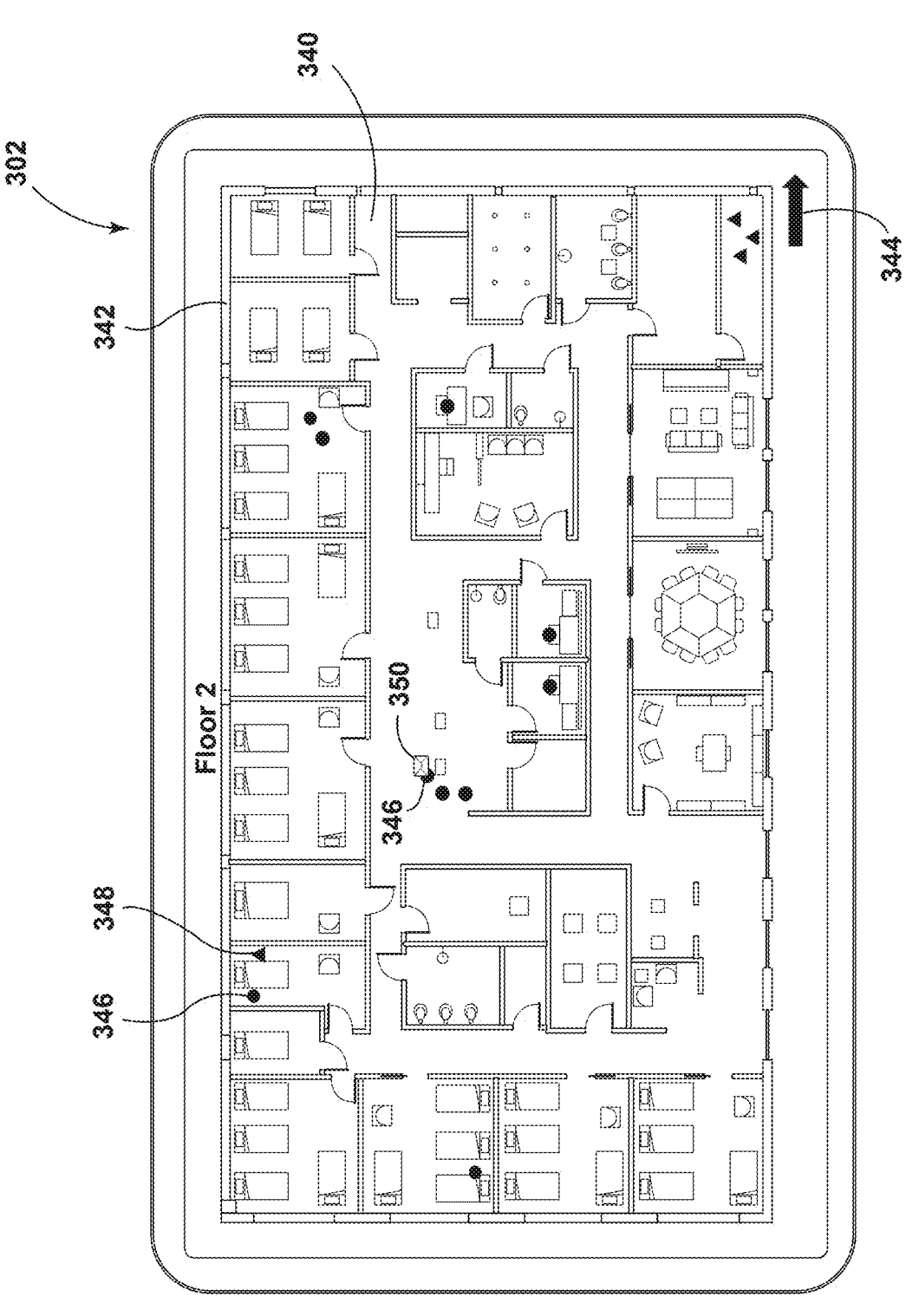
FIG. 13 is illustrative of an application interface with a graphical representation of a floor plan showing identifiers for asset tags and caregiver tags and an indicator for a message from one of the tags, according to the present disclosure.

With reference now to FIG. 13, the controller 28 (FIG. 3) is configured to generate a mapping screen 340, which is displayed on the application interface 302, to allow visual tracking of the tags 12 and messages 30 throughout the medical facility 40. A graphical representation of a floor plan 342 for the medical facility 40 may be displayed. Additional levels or floors may be viewed by selecting an arrow icon 344. The location of the caregiver tags 42 and the asset tags 44 may be indicated on the floor plan 342 via identifiers 346, 348, respectively. In the example illustrated in FIG. 13, the caregiver tags 42 are represented by the first identifier 346 (e.g., a circle) and the asset tags 44 are represented by the second identifier 348 (e.g., a triangle). The floor plan 342 may be continuously updated by the controller 28 in response to subsequent information from the receivers 26 and/or the tags 12.

Further, when button press information is communicated from one of the tags 12, the subsequent communication of the message 30 may appear as an indicator 350 on the floor plan 342. The indicator 350 may be disposed proximate to the identifier 346, 348 associated with the tag 12 that communicated the button press information. The indicator 350 may be generic to alert those viewing the application interface 302 that the message 30 has been sent in response to the button press information from the select tag 12. Additionally or alternatively, selection of the indicator 350 may display (e.g., in a pop-up graphic, in a separate screen, etc.) the message 30. In additional non-limiting examples where each message 30 is preset or categorized, each type of message 30 may be associated with a specific indicator 350, allowing the specific indicator 350 to be displayed proximate to the identifier 346, 348 of the tag 12. Accordingly, the indicator 350 may be indicative of any message 30 or a specific message 30.

Figure 14:
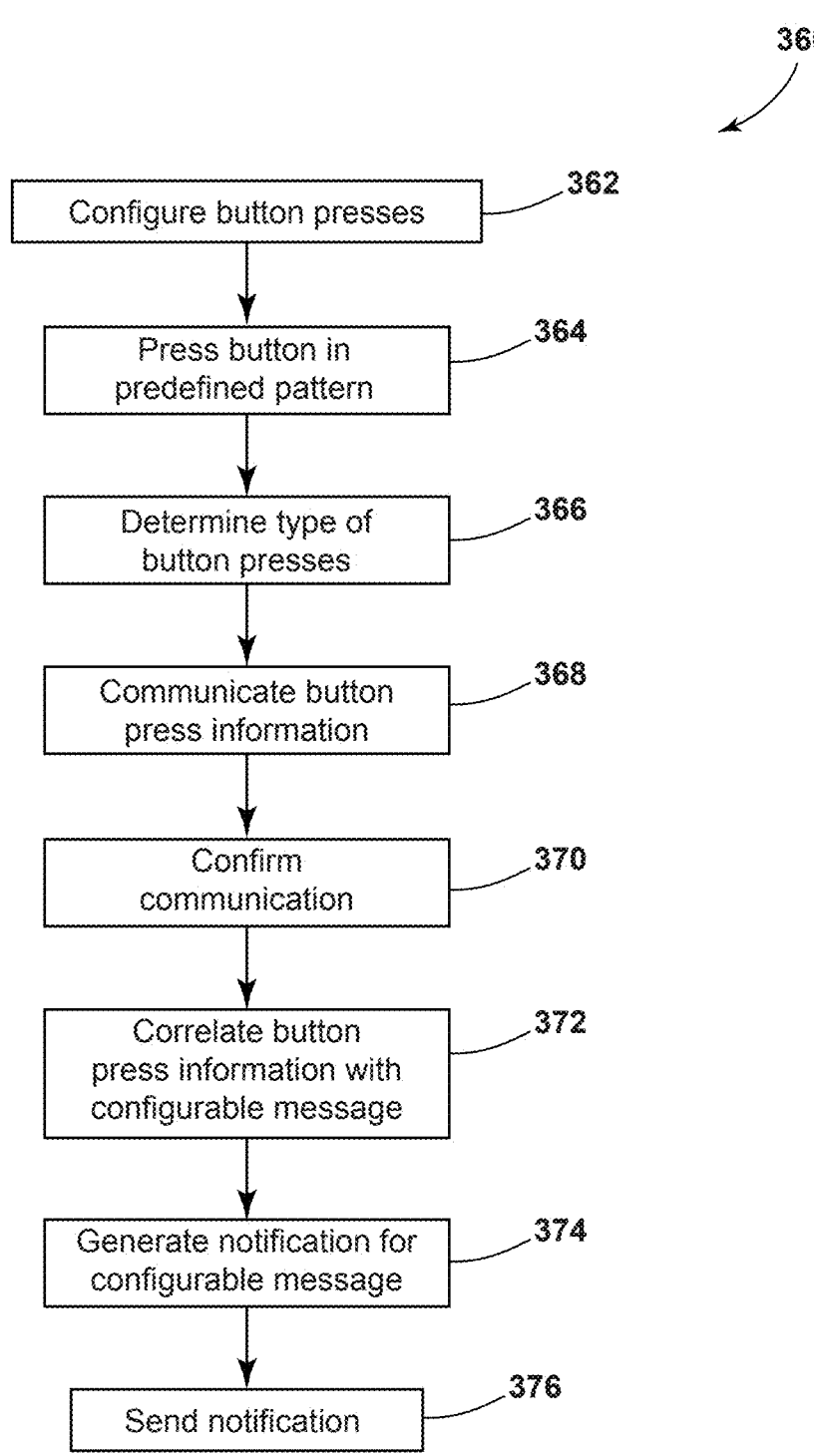
FIG. 14 is a flow diagram of a method of communicating messages with a locating system, according to the present disclosure.

Referring to FIG. 14, as well as FIGS. 1-13, a method 360 for communicating messages 30 via the locating system 10 includes step 362 of configuring the button presses. The caregiver or user may utilize the application interface 302 to enter the message-related input into the locating system 10 and assign certain functions or messages 30 to each type of button press for each button 16, 18 on each type of tag 12 within the locating system 10. The caregiver or user may input identification information (e.g., credentials) to authorize access to change the information for the messages 30. In certain aspects, administrators for the medical facility 40 may have access to change the messages 30 throughout the medical facility 40. Additionally or alternatively, where messages 30 can be personalized to certain caregivers, the individual caregivers may be able to change the messages 30 for their respective caregiver tag 42.

In step 364, the caregiver presses one or both buttons 16, 18 on the tag 12 in a predefined pattern or manner. The select combination or length of button presses correspond with the select message 30 or messages 30. In step 366, the types of button presses are measured or determined by the respective drivers 20 and communicated to the control units 22 of the tags 12.

In step 368, the control unit 22 is configured to communicate the button press information. The button press information with the tag signal may be communicated to the receiver 26 for which the tag 12 is positioned in the associated reception zone 134 and then to the controller 28. In such examples, the button press information is generally communicated via a single receiver 26. It is also contemplated that the button press information may be communicated utilizing more the one receiver 26. Alternatively, the button press information may be communicated to the controller 28 without the receiver 26.

In step 370, the controller 28 may confirm receipt of the communication about the button press information to the tag 12. For example, the indicator light 120, 260 of the respective tag 12 may illuminate in response to the confirmation. Other visual, tactile, or haptic modes may be utilized to confirm receipt of the button press information. The confirmation may be transmitted directly from the controller 28 to the tag 12, through the communication network 280 to the tag 12, or through the receivers 26 to the tag 12.

In step 372, the controller 28 is configured to correlate the button press information received from the tag 12 with the configurable message 30. In step 374, the controller 28 is configured to generate the notification 32 based on the message 30 or to include the message 30, and in step 376, the controller 28 is configured to send the notification 32 to the application interface 302 to be viewed by the caregiver. The message 30 may be sent to select people based on the assignment stored in the controller 28. For example, certain notifications 32 may be communicated to nurses, while others are communicated to technicians. Further, the station devices 306 or the status board 308 may show certain notifications 32, while others are viewable in an electronic medical record or patient profile viewable by the caregiver. It is understood that the steps 362-376 of the method 360 may be performed in any order, simultaneously, repeated, and/or omitted without departing the teachings provided herein.

Figure 15:
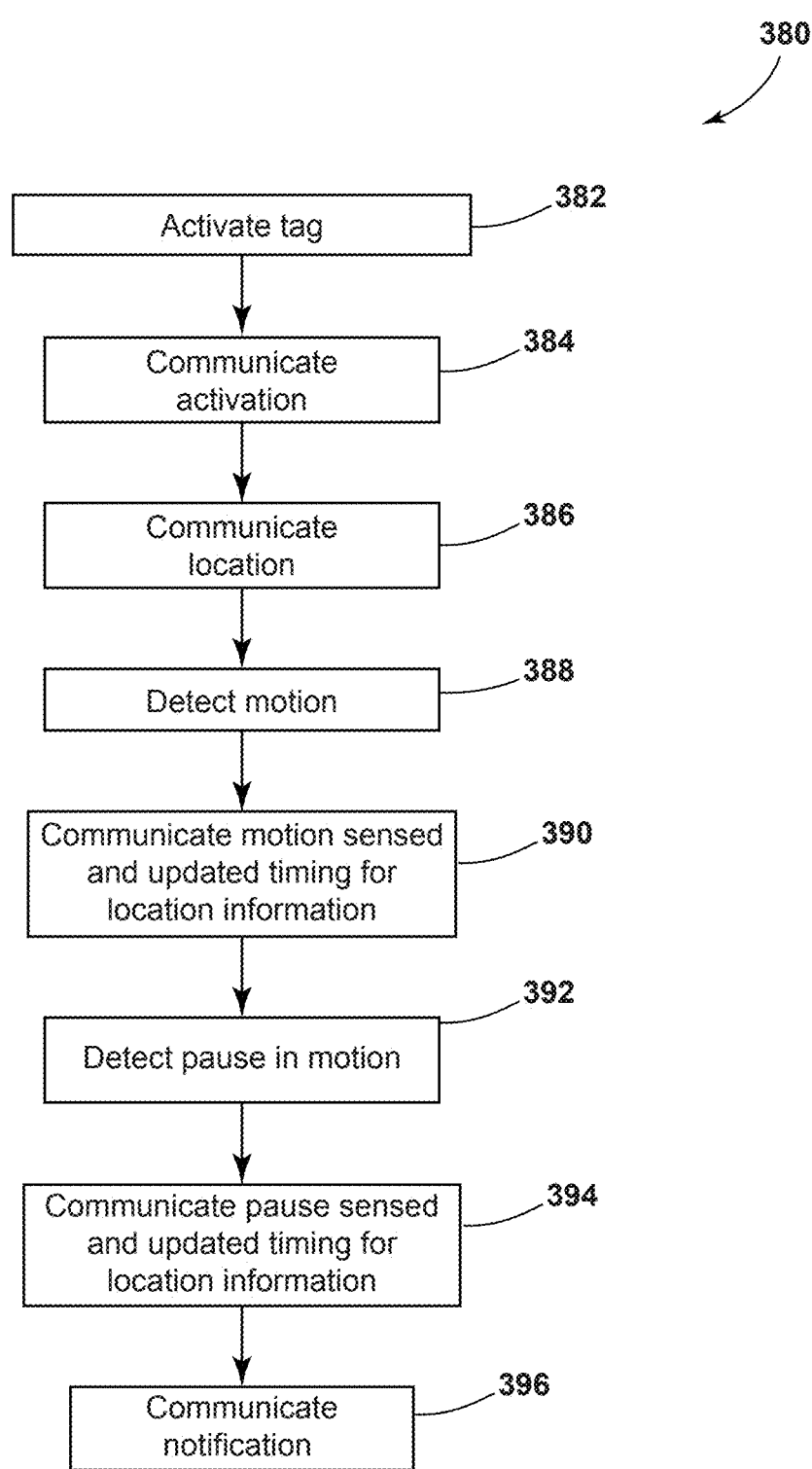
FIG. 15 is a flow diagram of a method of communicating location information with a locating system, according to the present disclosure.

Referring to FIG. 15, as well as FIGS. 1-14, a method 380 for communicating location information may occur separate from or in combination with the method 360 for communicating the message 30 via the locating system 10. The method 380 for communicating the location information includes step 382 of activating the tag 12. The tag 12 may be powered on and communicate the activation status to the controller 28. If the tag 12 is new, the tag 12 may be placed in a certification mode to determine whether the tag 12 is installed correctly. In the certification mode, the locating system 10 does not report the information associated with any button presses but provides verification that the communication from the tag 12 was received. Upon verification, the tag 12 is switched out of the certification mode to a fully activated state.

In step 384, the tag 12 is configured to communicate with the receiver 26. The tag 12 is configured to communicate the tag signal, including at least the tag ID, to any receivers 26 for which the tag 12 is positioned in the associated reception zone 134. The tag signal may also include the button press information. In step 386, the tag ID and the receiver ID are communicated by the receiver 26 to the controller 28. Additionally, in step 386, the controller 28 associates the receiver ID and the tag ID with various stored information (location, caregiver, equipment, etc.) to determine the location information for the select tag 12 and the person or equipment associated with the tag 12. In various aspects, the location information is determined using information received from more than one receiver 26, such as between two and four receivers 26. Using multiple receivers 26 may provide additional location information. However, it is contemplated that information from a single receiver 26 can be utilized to determine the location information without departing from the teachings herein.

In step 388, the motion sensor 314 is configured to sense motion of the tag 12. Based on the sensed motion, in step 390, the tag 12 is configured to communicate with the controller 28 that the tag 12 is in motion and the updated timing intervals in which the tag signal is to be communicated to the receiver 26 in response to the motion. In this way, the controller 28 is updated on when subsequent information should be received about the specific tag 12. The communication of the tag ID and the receiver ID continues at the updated timing intervals. Further, the location information is continually correlated with the stored information and updated within the locating system 10 in response to receiving each subsequent communication.

In step 392, the motion sensor 314 is configured to detect a pause in the motion. The pause may be for a predefined period of time where the tag 12 is considered to be stationary. In step 394, the tag 12 is configured to communicate the stop or pause in motion and the updated timing for communicating with the receivers 26 to the controller 28. The timing intervals for communicating the tag signal from the stationary tag 12 may be less than the timing intervals for the tag 12 in motion.

In step 396, the location information determined by the controller 28 is communicated to the application interface 302. The location information may be included in the notification 32, on the floor plan 342, or both. In this way, the location, as well as the movement of the tag 12, may be monitored throughout the medical facility 40. For example, the notification 32 may include that a certain asset tag 44 on the medical bed 142 has moved from one patient room to another patient room. Alternatively, the notification 32 may update the caregiver that the asset tag 44 that was previously in motion is now stationary. It is understood that the steps 382-396 of the method 380 may be performed in any order, simultaneously, repeated, and/or omitted without departing the teachings provided herein.

Figure 16:
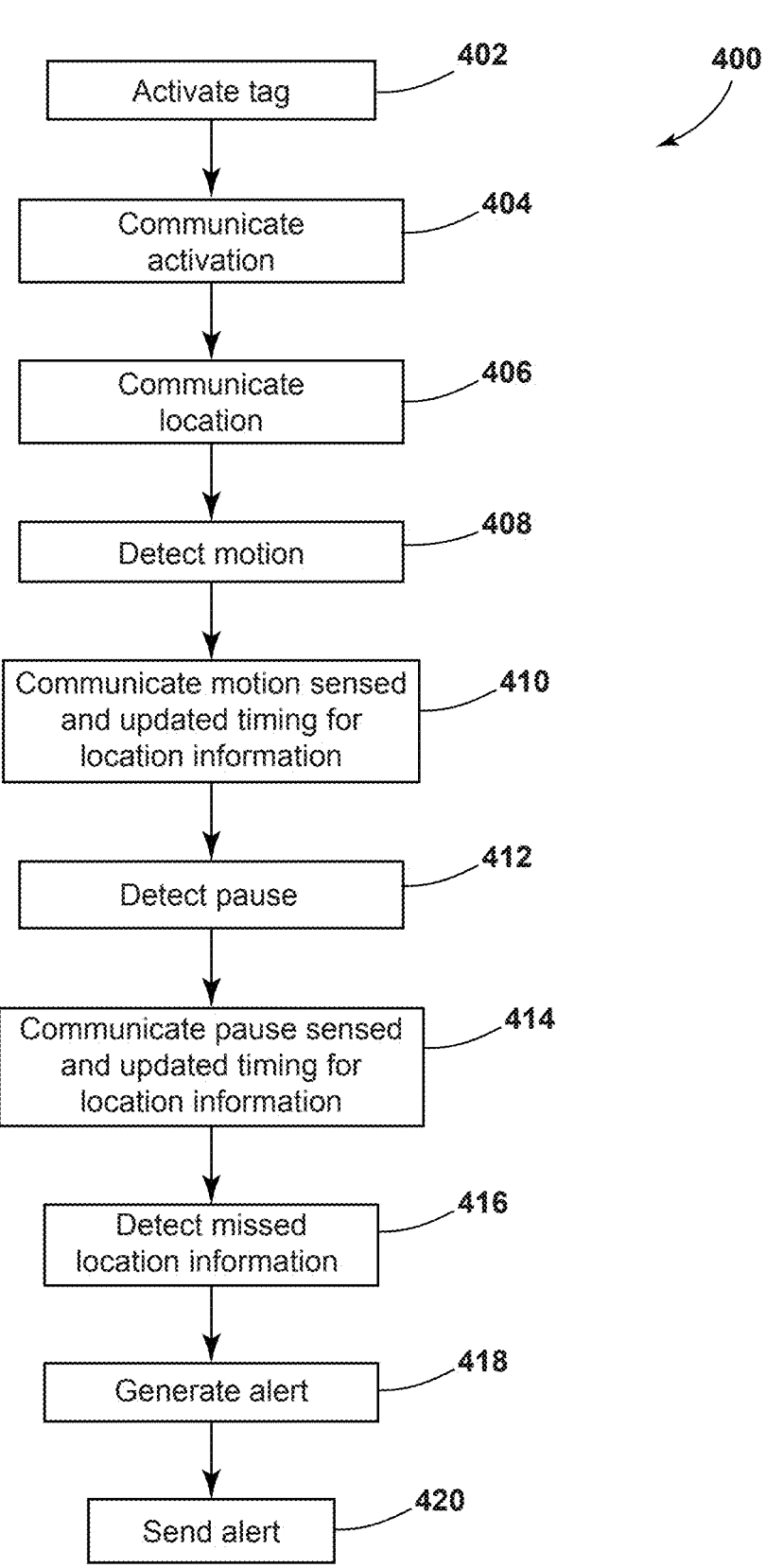
FIG. 16 is a flow diagram of a method of communicating location information with a locating system where a tag loses connectivity with the locating system, according to the present disclosure.

Referring to FIG. 16, as well as FIGS. 1-15, a method 400 of communicating the location information is similar to the method 380 illustrated in FIG. 15. The method 400 includes step 402 of activating the tag, step 404 of communicating the activation, and step 406 of communicating the tag ID and the receiver ID to the controller 28. Additionally, the method 400 includes step 408 of detecting motion and step 410 of communicating the updated timing intervals in response to the motion. Step 412 may include detecting a pause in the motion and step 414 includes communicating the updated intervals to the controller 28 in response to being stationary.

In step 416, the controller 28 is configured to determine whether or not the tag ID and the receiver ID were received at the predefined interval. The locating system 10 is programmed to monitor the receipt of information from the tags 12 at the timing intervals and any updated or subsequent timing intervals in response to the sensed motion. Additionally, in step 416, the controller 28 is configured to determine whether the tag 12 missed an interval or a predefined number of intervals for emitting the tag signal. In step 418, the controller 28 is configured to generate the alert 320 regarding the missed information. In step 420, the alert 320 is communicated to the application interface 302. It is understood that the steps 402-420 of the method 400 may be performed in any order, simultaneously, repeated, and/or omitted without departing the teachings provided herein.

With reference to FIGS. 1-16, the locating system 10 with the caregiver tags 42 and the asset tags 44 is utilized to monitor the location of each tag 12 as well as convey messages 30 via the tags 12. The communication of additional information and messages 30, aside from the location, may be advantageous for quickly and efficiently conveying select or predefined messages 30 to other caregivers or systems throughout the medical facility 40. The caregiver may send messages 30 via the tags 12 such as requesting a doctor, requesting security, or requesting cleaning. The tags 12 are also configured to update the controller 28 based on a change in circumstance or status change, which controls the generation of the notification 32 and the alert 320. For example, when the tag 12 is to be powered down or deactivated, the tag 12 communicates the deactivation to the controller 28 so the controller 28 does not generate the alert 320. Additionally, the tag 12 is configured to communicate at different timing intervals in response to sensed motion. The locating system 10 provides a system for monitoring the location of caregivers and equipment within the medical facility 40 in real time, while also communicating predefined messages 30 in response to button presses.

Use of the present device and system may provide for a variety of advantages. For example, the locating system 10 may be configurable by each medical facility 40 to customize and personalize the messages 30 sent via the tags 12. Further, the tags 12 may be utilized to convey multiple messages 30 based on the type of button presses. Additionally, the tags 12 are configured to update the locating system 10 on location (e.g., the tag ID through the receivers 26), message information, and motion information. Moreover, the indicator lights 120, 260 may indicate power level, confirmation from the controller 28, and confirmation of the type of button presses. Additional benefits or advantages may be realized and/or achieved.

Each of the controller 28 and the control units 22, 84, 210 disclosed herein may include various types of control circuitry, digital or analog, and may each include a processor 86, 212, 290, a microcontroller, an application specific integrated circuit (ASIC), or other circuitry configured to perform the various inputs or outputs, control, analysis, or other functions described herein. The memories 88, 214, 292 described herein may be implemented in a variety of volatile and nonvolatile memory formats. Routines 90, 216, 294 may include operating instructions to enable the various methods described herein.

The device and system disclosed herein is further summarized in the following paragraphs and is further characterized by any and all various aspects described herein and combinations thereof.

According to another aspect of the present disclosure, a locating system includes a tag with body that has a first button and a second button, a driver configured to determine a type of button press of at least one of the first button and the second button, and a control unit in communication with the driver. The control unit is configured to communicate the type of button press determined by the driver. The tag also includes a transmitter in communication with the control unit. At least one receiver is configured to selectively communicate with the transmitter. A controller is in communication with the receiver. The controller is configured to determine a location of the tag within a predefined area based on information from the at least one receiver, correlate the type of button press from the tag with a message, and generate a notification to communicate the message.

According to another aspect of the present disclosure, a controller is configured to generate a notification with message information based on a message correlated with a type of button press.

According to another aspect of the present disclosure, at least one receiver includes multiple receivers arranged in a predefined area. Each receiver has a reception zone for communicating with a transmitter.

According to another aspect of the present disclosure, a driver includes multiple first counters configured to adjust in response to a press of a first button and multiple second counters configured to adjust in response to a press of a second button.

According to another aspect of the present disclosure, a tag includes a motion sensor. A controller is configured to determine a location of the tag at different time intervals based on motion sensed by the motion sensor.

According to another aspect of the present disclosure, time intervals are first predefined intervals when a tag is in motion and second predefined intervals with the tag is stationary. The first predefined intervals are shorter than the second predefined intervals.

According to another aspect of the present disclosure, a tag is an asset tag and includes a bracket coupled to a body and configured to couple to a medical device and a tamper sensor configured to sense when the asset tag is coupled to the medical device.

According to another aspect of the present disclosure, an asset tag includes a tamper counter configured to adjust in response to a tamper sensor sensing an asset tag is removed from a medical device.

According to another aspect of the present disclosure, a tag is a caregiver tag having a charging port for charging a rechargeable power source.

According to another aspect of the present disclosure, at least one button includes a front button and a side button. A controller is configured to store a table that correlates a type of button press of a front button, a side button, and button press patterns with a message. The message correlated with the type of button press includes at least one of a request for cleaning, a request for maintenance, a request for a doctor, and a distress alert.

According to another aspect of the present disclosure, a locating system for a medical facility includes a tag with buttons and a driver configured to measure a type of a press of each button. The tag includes a control unit configured to communicate the type of button press. A controller is in communication with the tag. The controller is configured to store an assignment for each type of button press of each button, correlate the type of button press received from the tag with the assignment, and generate a notification with a message in response to the assignment.

According to another aspect of the present disclosure, a tag includes a driver having multiple counters. Each counter is configured to adjust in response to one type of button press for one button.

According to another aspect of the present disclosure, multiple counters include a first counter that adjusts in response to a first type of button press, a second counter that adjusts in response to a second type of button press, and a third counter that adjusts in response to a third type of button press.

According to another aspect of the present disclosure, a first type of button press is a single press for a first predefined period of time, a second type of button press is a double press, and a third type of button press is the single press for a second predefined period of time. The second predefined period of time is longer than the first predefined period of time.

According to another aspect of the present disclosure, a tag includes an indicator light configured to illuminate in response to a press of at least one button.

According to another aspect of the present disclosure, an indicator light is configured to illuminate in a pattern based on a type of button press.

According to another aspect of the present disclosure, a receiver is in communication with a transmitter of a tag. The receiver is configured to communicate receiver information and tag information to a controller.

According to another aspect of the present disclosure, a controller is configured to determine a location of a tag in a medical facility based on receiver information and tag information.

According to another aspect of the present disclosure, a controller is configured to generate a graphical representation of a floor plan of a medical facility and update an identifier on the floor plan in response to a location of a tag.

According to another aspect of the present disclosure, a caregiver tag for a locating system includes a front cover including a front button and a side button. A rear cover is coupled to the front cover to define an interior. A driver is disposed within the interior and configured to determine a type of button press of the front button and the side button. A transmitter is disposed within the interior. The transmitter is configured to communicate a tag signal. A motion sensor is disposed within the interior and is configured to sense movement of said caregiver tag. A control unit is in communication with the motion sensor.

According to another aspect of the present disclosure, a transmitter is configured to communicate a tag signal at first intervals when a motion sensor senses movement.

According to another aspect of the present disclosure, a transmitter is configured to communicate a tag signal at second intervals when a caregiver tag is stationary as sensed by a motion sensor. The second intervals are longer than first intervals.

According to another aspect of the present disclosure, a control unit is configured to communicate an adjustment of time intervals for communicating a tag signal to a controller of a locating system based on a change in motion sensed by a motion sensor.

According to another aspect of the present disclosure, a driver includes multiple front counters each configured to adjust in response to one type of front button press of a front button and multiple side counters configured to adjust in response to one type of side button press of a side button.

According to another aspect of the present disclosure, an asset tag for a locating system includes a front cover that has a button. A rear cover is coupled to the front cover to define an interior. A bracket is coupled to the rear cover for engaging equipment. A tamper sensor is operably coupled to the bracket. The tamper sensor is configured to sense when the bracket is engaged with the equipment. A driver is disposed within the interior and configured to determine a type of button press for the button. A transmitter is disposed within the interior and configured to communicate a tag signal.

According to another aspect of the present disclosure, a driver includes a tamper counter configured to adjust when a tamper sensor senses a bracket is disengaged from equipment.

According to another aspect of the present disclosure, a motion sensor is configured to sense motion of an asset tag, and a control unit is configured to communicate updated timing intervals for communicating a tag signal in response to the sensed motion.

According to another aspect of the present disclosure, a control unit is configured to communicate a status change of an asset tag to a controller of a locating system.

According to another aspect of the present disclosure, a status change includes at least one of a change in motion, activation, and deactivation.

According to another aspect of the present disclosure, a locating system for a medical facility includes at least one tag including a body having at least one button, a driver configured to measure a type of button press for the at least one button, and a transmitter configured to communicate a tag signal. A receiver is disposed in said medical facility. The receiver defines a reception zone for selectively communicating with the transmitter. A controller is in communication with the receiver. The controller is configured to determine a location of the at least one tag based on information from the receiver, correlate a message with the type of button press from the at least one tag, and generate a notification with message information.

According to another aspect of the present disclosure, at least one tag includes a caregiver tag configured to be worn by a caregiver and an asset tag configured to be coupled to equipment.

According to another aspect of the present disclosure, at least one tag includes a control unit in communication with a controller. The control unit is configured to communicate time intervals for communicating a tag signal.

According to another aspect of the present disclosure, a controller is configured to determine whether a tag signal was received at each time interval.

According to another aspect of the present disclosure, a controller is configured to generate an alert when the controller is free of a tag signal for a predefined number of time intervals.

According to another aspect of the present disclosure, a controller is configured to generate a graphical representation of a floor plan of a medical facility. The graphical representation includes an identifier for at least one tag.

According to another aspect of the present disclosure, a graphical representation includes an indicator indicative of a message from at least one tag.

According to another aspect of the present disclosure, at least one tag includes a motion sensor. A tag signal is communicated at intervals configured to be adjusted in response to sensed motion.

According to another aspect of the present disclosure, a controller is configured to store a table that correlates a type of button press with a message.

According to another aspect of the present disclosure, a message includes at least one of a request for cleaning, a request for maintenance, a request for a doctor, and a distress alert.

According to another aspect of the present disclosure, button press information communicated to a controller includes a timestamp of a button press.

According to another aspect of the present disclosure, a tag signal includes a button counter value. The button counter value is transmitted from at least one tag at predefined intervals.

According to another aspect of the present disclosure, a controller is configured to compare a first button counter value received from at least one tag with a subsequent button counter value received from the at least one tag and determine a type of button press based on a difference between the first button counter value and the subsequent button counter value.

According to another aspect of the present disclosure, a controller is configured to determine a pattern of button presses since a tag signal was received based on a difference between a first button counter value and a subsequent button counter value.

According to another aspect of the present disclosure, at least one button includes a front button and a side button.

According to another aspect of the present disclosure, a locating system includes a controller configured to determine a location of a tag within a predefined area, receive information regarding movement of the tag within the predefined area, receive timing intervals for receiving tag information in response to the movement, receive button press information from the tag, correlate the button press information to a message, and generate a notification in response to the button press information.

A locating means includes a communication means including a body having a first button and a second button and a measurement means configured to determine a type of button press of at least one of the first button and the second button. A first control means is in communication with the measurement means. The first control means is configured to communicate the type of button press determined by the measurement means. A transmission means is in communication with the first control means. A receiving means is configured to selectively communicate with the transmission means. A second control means is in communication with the receiving means. The second control means is configured to determine a location of the communication means within a predefined area based on information from the receiving means, correlate the type of button press from the communication means with a message, and generate a notification to communicate the message.

Related applications, for example those listed herein, are fully incorporated by reference. Assertions within the related applications are intended to contribute to the scope and interpretation of the information disclosed herein. Any changes between any of the related applications and the present disclosure are not intended to limit the scope or interpretation of the information disclosed herein, including the claims. Accordingly, the present application includes the scope and interpretation of the information disclosed herein as well as the scope and interpretation of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A locating system for a medical facility, comprising:
   a tag including:
      a body including a button and defining an interior;
      at least one counter disposed within the interior and operably coupled with the button, wherein the at least one counter is configured to adjust in response to a button press of the button;
      a driver disposed within the interior and operably coupled with the at least one counter;
      a control unit communicatively coupled with the driver, wherein at least one of the control unit and the driver is configured to determine a type of button press in response to adjustment of the at least one counter; and
      a transmitter communicatively coupled with the control unit and configured to communicate a tag signal;
   a receiver configured to selectively communicate with the transmitter in a reception zone of the receiver; and
   a controller in communication with the receiver, wherein the controller is configured to:
      determine a location of the tag based on information from the receiver;
      receive the tag signal including the type of button press;
      correlate the tag signal with at least one of equipment and a caregiver with which the tag is associated;
      correlate a message with the type of button press from the tag; and
      generate a notification with information based on the message correlated with the type of button press.

2. The locating system of claim 1, wherein the driver is configured to determine a button counter value of the at least one counter, and wherein the tag signal received by the controller includes the button counter value.

3. The locating system of claim 2, wherein the controller is configured to:
   compare the button counter value received in the tag signal with previously received button information;
   determine whether the button counter value is different than the previously received button information; and
   correlate the message in response to the button counter value being different than the previously received button information.

4. The locating system of claim 1, wherein the at least one counter includes multiple counters, and wherein each of the multiple counters is configured to adjust in response to a different one of the type of button press.

5. The locating system of claim 1, wherein the control unit is in communication with the controller, and wherein the control unit is configured to communicate time intervals to the controller for communicating the tag signal, and further wherein the controller is configured to determine whether the tag signal was received at each time interval.

6. The locating system of claim 1, wherein the tag includes a motion sensor, and wherein the tag signal is communicated at intervals configured to be adjusted in response to sensed motion.

7. The locating system of claim 1, wherein the tag includes:
   a tamper sensor configured to extend through the body, and wherein the tamper sensor is adjustable to be compressed against the equipment and released when removed from the equipment; and
   a tamper counter operably coupled to the tamper sensor and the driver, wherein the tamper counter is configured to adjust in response to adjustment of the tamper sensor, and wherein the driver is configured to monitor adjustment of the tamper counter.

8. The locating system of claim 7, wherein the message includes an indication that the tag is being removed from the equipment.

9. A locating and tracking system, comprising:

a tag configured to couple with equipment, the tag including:

a body having a front button;

button counters operably coupled with the front button, wherein each counter is configured to adjust in response to a predefined button press;

a tamper sensor configured to move between a first position when engaging the equipment and a second position when removed from the equipment;

a tamper counter configured to adjust in response to movement of the tamper sensor between the first and second positions;

a driver configured to determine adjustment of the button counters and the tamper counter;

a control unit in communication with the driver, wherein the control unit is configured to determine a type of button press in response to adjustment of at least one of the button counters; and a transmitter in communication with the control unit, the transmitter configured to communicate a tag signal with the type of button press and the adjustment of the tamper counter; and a controller configured to:

receive an indication that the tamper sensor is adjusted to the first position;

receive an indication that the tamper sensor is adjusted to the second position;

receive the type of button press;

correlate the type of button press from the tag with a message; and generate a notification with message information based on the message correlated with the type of button press.

10. The locating and tracking system of claim 9, further comprising:

a receiver communicatively coupled with the tag and the controller, wherein the controller is configured to determine a location of the tag within a predefined area based on information from the receiver.

11. The locating and tracking system of claim 9, wherein the control unit is configured to:

determine whether the tamper sensor is adjusted to the second position; and determine how often the tamper sensor is adjusted between the first and second positions.

12. The locating and tracking system of claim 9, wherein the tag signal is free of information related to the adjustment of the tamper counter in response to the message including an indication that the tag is being removed from the equipment.

13. The locating and tracking system of claim 9, wherein the tag includes a motion sensor, and wherein the controller is configured to determine a location of the tag at different time intervals based on motion sensed by the motion sensor.

14. The locating and tracking system of claim 9, wherein the tag signal includes button counter values for the button counters, and wherein the controller is configured to:

compare the button counter values received in the tag signal with previously received button counter values; and correlate the button counter values with the message in response to a difference between the button counter values and the previously received button counter values.

* * * * *